United States Patent
Cam et al.

(10) Patent No.: US 11,779,437 B2
(45) Date of Patent: Oct. 10, 2023

(54) TREATMENT OF TEMPEROMANDIBULAR JOINT DYSFUNCTION WITH ALIGNER THERAPY

(71) Applicant: Align Technology, Inc., San Jose, CA (US)

(72) Inventors: Bruce Cam, San Jose, CA (US); John Y. Morton, San Jose, CA (US); Vadim Matov, San Jose, CA (US); Jun Sato, San Jose, CA (US)

(73) Assignee: Align Technology, Inc., San Jose, CA (US)

( * ) Notice: Subject to any disclaimer, the term of this patent is extended or adjusted under 35 U.S.C. 154(b) by 259 days.

(21) Appl. No.: 16/024,292

(22) Filed: Jun. 29, 2018

(65) Prior Publication Data
US 2019/0000592 A1    Jan. 3, 2019

Related U.S. Application Data

(60) Provisional application No. 62/527,856, filed on Jun. 30, 2017.

(51) Int. Cl.
*A61C 7/08* (2006.01)
*A61F 5/56* (2006.01)
*A61C 7/00* (2006.01)
*A61C 9/00* (2006.01)
*A63B 71/08* (2006.01)

(52) U.S. Cl.
CPC ............... *A61C 7/08* (2013.01); *A61C 7/002* (2013.01); *A61C 9/0046* (2013.01); *A61F 5/566* (2013.01); *A63B 71/085* (2013.01)

(58) Field of Classification Search
CPC ........ A61F 2/3099; A61F 5/566; A61C 7/002; A61C 7/08; A61C 9/0046; A61C 9/0053
See application file for complete search history.

(56) References Cited

U.S. PATENT DOCUMENTS

| | | |
|---|---|---|
| 2,467,432 A | 4/1949 | Kesling |
| 3,407,500 A | 10/1968 | Kesling |
| (Continued) | | |

FOREIGN PATENT DOCUMENTS

| | | |
|---|---|---|
| AU | 3031677 A | 5/1979 |
| AU | 517102 B2 | 7/1981 |
| (Continued) | | |

OTHER PUBLICATIONS

AADR. American Association for Dental Research, Summary of Activities, Mar. 20-23, 1980, Los Angeles, CA, p. 195.

(Continued)

*Primary Examiner* — Jacqueline T Johanas
*Assistant Examiner* — Shannel Nicole Belk
(74) *Attorney, Agent, or Firm* — Wilson Sonsini Goodrich & Rosati

(57) ABSTRACT

Methods and systems are provided for diagnosing and generating a treatment plan for temporomandibular joint dysfunction where a polymeric shell appliance is utilized to generate one or more activation forces that facilitate tooth movement. The polymeric shell appliances may comprise one or more tooth receiving cavities, in which each of the plurality of tooth receiving cavities is shaped and arranged to provide a counter moment of each of the plurality of teeth.

12 Claims, 11 Drawing Sheets

(56) References Cited

U.S. PATENT DOCUMENTS

| | | |
|---|---|---|
| 3,600,808 A | 8/1971 | Reeve |
| 3,660,900 A | 5/1972 | Andrews |
| 3,683,502 A | 8/1972 | Wallshein |
| 3,738,005 A | 6/1973 | Cohen et al. |
| 3,860,803 A | 1/1975 | Levine |
| 3,916,526 A | 11/1975 | Schudy |
| 3,922,786 A | 12/1975 | Lavin |
| 3,950,851 A | 4/1976 | Bergersen |
| 3,983,628 A | 10/1976 | Acevedo |
| 4,014,096 A | 3/1977 | Dellinger |
| 4,195,046 A | 3/1980 | Kesling |
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,478,580 A | 10/1984 | Barrut |
| 4,500,294 A | 2/1985 | Lewis |
| 4,504,225 A | 3/1985 | Yoshii |
| 4,505,673 A | 3/1985 | Yoshii |
| 4,526,540 A | 7/1985 | Dellinger |
| 4,575,330 A | 3/1986 | Hull |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | Van Der Zel |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,328,362 A | 7/1994 | Watson et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,382,164 A | 1/1995 | Stern |
| 5,395,238 A | 3/1995 | Andreiko et al. |
| 5,431,562 A | 7/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| RE35,169 E | 3/1996 | Lemchen et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern |
| 5,562,448 A | 10/1996 | Mushabac |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre, Sr. |
| 5,621,648 A | 4/1997 | Crump |
| 5,645,420 A | 7/1997 | Bergersen |
| 5,645,421 A | 7/1997 | Slootsky |
| 5,655,653 A | 8/1997 | Chester |
| 5,683,243 A | 11/1997 | Andreiko et al. |
| 5,692,894 A | 12/1997 | Schwartz et al. |
| 5,725,376 A | 3/1998 | Poirier |
| 5,725,378 A | 3/1998 | Wang |
| 5,733,126 A | 3/1998 | Andersson et al. |
| 5,740,267 A | 4/1998 | Echerer et al. |
| 5,742,700 A | 4/1998 | Yoon et al. |
| 5,799,100 A | 8/1998 | Clarke et al. |
| 5,800,174 A | 9/1998 | Andersson |
| 5,823,778 A | 10/1998 | Schmitt et al. |
| 5,848,115 A | 12/1998 | Little et al. |
| 5,857,853 A | 1/1999 | Van et al. |
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 6,015,289 A | 1/2000 | Andreiko et al. |
| 6,044,309 A | 3/2000 | Honda |
| 6,049,743 A | 4/2000 | Baba |
| 6,062,861 A | 5/2000 | Andersson |
| 6,068,482 A | 5/2000 | Snow |
| 6,099,314 A | 8/2000 | Kopelman et al. |
| 6,123,544 A | 9/2000 | Cleary |
| 6,152,731 A | 11/2000 | Jordan et al. |
| 6,183,248 B1 | 2/2001 | Chishti et al. |
| 6,190,165 B1 | 2/2001 | Andreiko et al. |
| 6,217,325 B1 | 4/2001 | Chishti et al. |
| 6,217,334 B1 | 4/2001 | Hultgren |
| 6,244,861 B1 | 6/2001 | Andreiko et al. |
| 6,309,215 B1 | 10/2001 | Phan et al. |
| 6,315,553 B1 | 11/2001 | Sachdeva et al. |
| 6,322,359 B1 | 11/2001 | Jordan et al. |
| 6,350,120 B1 | 2/2002 | Sachdeva et al. |
| 6,382,975 B1 | 5/2002 | Poirier |
| 6,398,548 B1 | 6/2002 | Muhammad et al. |
| 6,402,707 B1 | 6/2002 | Ernst |
| 6,482,298 B1 | 11/2002 | Bhatnagar |
| 6,524,101 B1 | 2/2003 | Phan et al. |
| 6,554,611 B2 | 4/2003 | Shishti et al. |
| 6,572,372 B1 | 6/2003 | Phan et al. |
| 6,629,840 B2 | 10/2003 | Chishti et al. |
| 6,705,863 B2 | 3/2004 | Phan et al. |
| 6,722,880 B2 | 4/2004 | Chishti et al. |
| 6,749,414 B1 | 6/2004 | Hanson et al. |
| 7,892,474 B2 | 2/2011 | Shkolnik et al. |
| 2002/0006597 A1 | 1/2002 | Andreiko et al. |
| 2003/0009252 A1 | 1/2003 | Pavlovskaia et al. |
| 2003/0139834 A1 | 7/2003 | Nikolskiy et al. |

(56) References Cited

U.S. PATENT DOCUMENTS

| | | | |
|---|---|---|---|
| 2003/0224311 A1 | 12/2003 | Cronauer | |
| 2004/0128010 A1 | 7/2004 | Pavlovskaia et al. | |
| 2005/0055118 A1 | 3/2005 | Nikolskiy et al. | |
| 2009/0316966 A1* | 12/2009 | Marshall | A61B 6/5217 382/128 |
| 2014/0061974 A1 | 3/2014 | Tyler et al. | |
| 2014/0265034 A1 | 9/2014 | Dudley | |
| 2015/0000677 A1* | 1/2015 | Magness | A61F 5/566 128/861 |
| 2015/0075542 A1* | 3/2015 | Robichaud | A61F 5/566 128/861 |
| 2015/0097315 A1 | 4/2015 | Desimone et al. | |
| 2015/0097316 A1 | 4/2015 | Desimone et al. | |
| 2015/0102532 A1 | 4/2015 | Desimone et al. | |
| 2015/0238280 A1* | 8/2015 | Wu | A61C 7/08 433/6 |
| 2015/0238283 A1* | 8/2015 | Tanugula | A61C 7/08 433/6 |
| 2016/0135925 A1* | 5/2016 | Mason | G06F 19/00 703/2 |
| 2016/0199216 A1* | 7/2016 | Cam | A61F 5/566 128/848 |
| 2018/0078342 A1* | 3/2018 | Gardner | A61C 7/36 |
| 2018/0078344 A1* | 3/2018 | Falkel | A61C 7/36 |
| 2018/0153733 A1 | 6/2018 | Kuo | |

FOREIGN PATENT DOCUMENTS

| | | |
|---|---|---|
| AU | 5598894 A | 6/1994 |
| CA | 1121955 A | 4/1982 |
| CN | 101636122 A | 1/2010 |
| CN | 106691608 A | 5/2017 |
| CN | 206463067 U | 9/2017 |
| DE | 2749802 A1 | 5/1978 |
| DE | 69327661 T2 | 7/2000 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 1/2000 |
| EP | 0774933 B1 | 12/2000 |
| EP | 0731673 B1 | 5/2001 |
| ES | 463897 A1 | 1/1980 |
| FR | 2369828 A1 | 6/1978 |
| FR | 2652256 A1 | 3/1991 |
| GB | 1550777 A | 8/1979 |
| JP | S5358191 A | 5/1978 |
| JP | H0428359 A | 1/1992 |
| JP | H08508174 A | 9/1996 |
| WO | WO-9008512 A1 | 8/1990 |
| WO | WO-9104713 A1 | 4/1991 |
| WO | WO-9410935 A1 | 5/1994 |
| WO | WO-9832394 A1 | 7/1998 |
| WO | WO-9844865 A1 | 10/1998 |
| WO | WO-9858596 A1 | 12/1998 |
| WO | WO-2018057547 A1 | 3/2018 |
| WO | WO-2019006416 A1 | 1/2019 |

OTHER PUBLICATIONS

Alcaniz, et aL, "An Advanced System for the Simulation and Planning of Orthodontic Treatments," Karl Heinz Hohne and Ron Kikinis (eds.), Visualization in Biomedical Computing, 4th Intl. Conf., VBC '96, Hamburg, Germany, Sep. 22-25, 1996, Springer-Verlag, pp. 511-520.

Alexander et al., "The DigiGraph Work Station Part 2 Clinical Management," JCO, pp. 402-407 (Jul. 1990).

Altschuler, "3D Mapping of Maxillo-Facial Prosthesis," AADR Abstract #607, 2 pages total, (1980).

Altschuler et al., "Analysis of 3-D Data for Comparative 3-D Serial Growth Pattern Studies of Oral-Facial Structures," IADR Abstracts, Program and Abstracts of Papers, 57th General Session, IADR Annual Session, Mar. 29, 1979-Apr. 1, 1979, New Orleans Marriot, Journal of Dental Research, vol. 58, Jan. 1979, Special Issue A, p. 221.

Altschuler et al., "Laser Electro-Optic System for Rapid Three-Dimensional (3D) Topographic Mapping of Surfaces," Optical Engineering, 20(6):953-961 (1981).

Altschuler et al., "Measuring Surfaces Space-Coded by a Laser-Projected Dot Matrix," SPIE Imaging Applications for Automated Industrial Inspection and Assembly, vol. 182, p. 187-191 (1979).

Andersson et al., "Clinical Results with Titanium Crowns Fabricated with Machine Duplication and Spark Erosion," Acta. Odontol. Scand., 47:279-286 (1989).

Andrews, The Six Keys to Optimal Occlusion Straight Wire, Chapters, pp. 13-24 (1989).

Bartels, et al., An Introduction to Splines for Use in Computer Graphics and Geometric Modeling, Morgan Kaufmann Publishers, pp. 422-425 (1987).

Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of Ill., Aug. 26-30, 1975, pp. 142-166.

Baumrind et al., "A Stereophotogrammetric System for the Detection of Prosthesis Loosening in Total Hip Arthroplasty," NATO Symposium on Applications of Human Biostereometrics, Jul. 9-13, 1978, SPIE, vol. 166, pp. 112-123.

Baumrind et al., "Mapping the Skull in 3-D," reprinted from J. Calif. Dent. Assoc., 48(2), 11 pages total, (1972 Fall Issue).

Baumrind, "Integrated Three-Dimensional Craniofacial Mapping: Background, Principles, and Perspectives," Semin, in Orthod., 7(4):223-232 (Dec. 2001).

Begole et al., "A Computer System for the Analysis of Dental Casts," The Angle Orthod., 51(3):253-259 (Jul. 1981).

Bernard et al., "Computerized Diagnosis in Orthodontics for Epidemiological Studies: A Progress Report," Abstract, J. Dental Res. Special Issue, vol. 67, p. 169, paper presented at International Association for Dental Research 66th General Session, Mar. 9-13, 1988, Montreal, Canada.

Bhatia et al., "A Computer-Aided Design for Orthognathic Surgery," Br. J. Oral Maxillofac. Surg., 22:237-253 (1984).

Biggerstaff, "Computerized Diagnostic Setups and Simulations," Angle Orthod., 40(1):28-36 (Jan. 1970).

Biggerstaff et al., "Computerized Analysis of Occlusion in the Postcanine Dentition," Am. J. Orthod., 61(3): 245-254 (Mar. 1972).

Biostar Opeation & Training Manual. Great Lakes Orthodontics, Ltd. 199 Fire Tower Drive, Tonawanda, New York. 14150-5890, 20 pages total (1990).

Blu, et al., "Linear interpolation revitalized", IEEE Trans. Image Proc., 13(5):710-719 (May 2004.

Bourke, "Coordinate System Transformation," (Jun. 1996), p. 1, retrieved from the Internet Nov. 5, 2004, URL< http://astronomy.swin.edu.au/-pbourke/prolection/coords>.

Boyd et al., "Three Dimensional Diagnosis and Orthodontic Treatment of Complex Malocclusions With the Invisalipn Appliance," Semin. Orthod., 7(4):274-293 (Dec. 2001).

Brandestini et al., "Computer Machined Ceramic Inlays: In Vitro Marginal Adaptation," J. Dent. Res. Special Issue, Abstract 305, vol. 64, p. 208 (1985).

Brook et al., "An Image Analysis System for the Determination of Tooth Dimensions from Study Casts: Comparison with Manual Measurements of Mesio-distal Diameter," J. Dent. Res., 65(3):428-431 (Mar. 1986).

Burstone et al., Precision Adjustment of the Transpalatal Lingual Arch: Computer Arch Form IN Predetermination, Am, Journal of Orthodontics, vol. 79, No. 2 (Feb. 1981), pp. 115-133.

Burstone (interview), "Dr. Charles J. Burstone on The Uses of the Computer in Orthodontic Practice (Part 1)," J. Clin. Orthod., 13(7):442-453 (Jul. 1979).

Burstone (interview), "Dr. Charles J. Burstone on The Uses of the Computer in Orthodontic Practice (Part 2)," J. Clin. Orthod., 13(8):539-551 (Aug. 1979).

(56) References Cited

OTHER PUBLICATIONS

Cardinal Industrial Finishes, Powder Coatings information posted at< http://www.cardinalpaint.com> on Aug. 25, 2000, 2 pages.
Carnaghan, "An Alternative to Holograms for the Portrayal of Human Teeth," 4th Int'l. Conf. on Holographic Systems, Components and Applications, Sep. 15, 1993, pp. 228-231.
Chaconas et al., "The DigiGraph Work Station, Part 1, Basic Concepts," JCO, pp. 360-367 (Jun. 1990).
Chafetz et al., "Subsidence of the Femoral Prosthesis, A Stereophotogrammetric Evaluation," Clin. Orthop. Relat. Res., No. 201, pp. 60-67 (Dec. 1985).
Chiappone, (1980). Constructing the Gnathologic Setup and Positioner, J. Clin. Orthod, vol. 14, pp. 121-133.
Cottingham, (1969). Gnathologic Clear Plastic Positioner, Am. J. Orthod, vol. 55, pp. 23-31.
Crawford, "CAD/CAM in the Dental Office: Does It Work?", Canadian Dental Journal, vol. 57, No. 2, pp. 121-123 (Feb. 1991).
Crawford, "Computers in Dentistry: Part 1 CAD/CAM: The Computer Moves Chairside" Part 2 F. Duret—A Man with a Vision, "Part 3 The Computer Gives New Vision—Literally," Part 4 Bytes 'N Bites—The Computer Moves from the Front Desk to the Operatory, Canadian Dental Journal, vol. 54 (9), pp. 661-666 (1988).
Crooks, "CAD/CAM Comes to USC," USC Dentistry, pp. 14-17 (Spring 1990).
Cureton, Correcting Malaligned Mandibular Incisors with Removable Retainers, J. Clin. Orthod, vol. 30, No. 7 (1996) pp. 390-395.
Curry et al., "Integrated Three-Dimensional Craniofacial Mapping at the Craniofacial Research Instrumentation Laboratory/University of the Pacific," Semin. Orthod., 7(4):258-265 (Dec. 2001).
Cutting et a/., "Three-Dimensional Computer-Assisted Design of Craniofacial Surgical Procedures: Optimization and Interaction with Cephalometric and CT-Based Models," Plast. 77(6):877-885 (Jun. 1986).
DCS Dental AG, "The CAD/CAM 'DCS Titan System' for Production of Crowns/Bridges," DSC Production AG, pp. 1-7 (Jan. 1992.
Definition for gingiva. Dictionary.com p. 1-3. Retrieved from the internet Nov. 5, 2004< http://reference.com/search/search?q=gingiva>.
Defranco et al., "Three-Dimensional Large Displacement Analysis of Orthodontic Appliances," J. Biomechanics, 9:793-801 (1976).
Dental Institute University of Zurich Switzerland, Program for International Symposium JD on Computer Restorations: State of the Art of the CEREC-Method, May 1991, 2 pages total.
Dentrac Corporation, Dentrac document, pp. 4-13 (1992).
Dent-X posted on Sep. 24, 1998 at< http://www.dent-x.com/DentSim.htm>, 6 pages.
Doyle, "Digital Dentistry," Computer Graphics World, pp. 50-52, 54 (Oct. 2000).
DuraClearTM product information, Allesee Orthodontic Appliances-Pro Lab, 1 page (1997).
Duret et al., "CAD/CAM Imaging in Dentistry," Curr. Opin. Dent., 1:150-154 (1991).
Duret et al, "CAD-CAM in Dentistry," J. Am. Dent. Assoc. 117:715-720 (Nov. 1988).
Duret, "The Dental CAD/CAM, General Description of the Project," Hennson International Product Brochure, 18 pages total, Jan. 1986.
DURET,"Vers Une Prosthese Informatisee," (English translation attached), Tonus, vol. 75, pp. 55-57 (Nov. 15, 1985).
Economides, "The Microcomputer in the Orthodontic Office," JCO, pp. 767-772 (Nov. 1979).
Elsasser, Some Observations on the History and Uses of the Kesling Positioner, Am. J. Orthod. (1950) 36:368-374.
English translation of Japanese Laid-Open Publication No. 63-11148 to inventor T. Ozukuri (Laid-Open on Jan. 18, 1998) pp. 1-7.
Felton et al., "A Computerized Analysis of the Shape and Stability of Mandibular Arch Form," Am. J. Orthod. Dentofacial Orthop., 92(6):478-483 (Dec. 1987).

Friede et al., "Accuracy of Cephalometric Prediction in Orthognathic Surgery," Abstract of Papers, J. Dent. Res., 70:754-760 (1987).
Futterling et a/., "Automated Finite Element Modeling of a Human Mandible with Dental Implants," JS WSCG '98—Conference Program, retrieved from the Internet:< http://wscg.zcu.cz/wscg98/papers98/Strasser 98.pdf>, 8 pages.
Gao et al., "3-D element Generation for Multi-Connected Complex Dental and Mandibular Structure," Proc. Intl Workshop on Medical Imaging and Augmented Reality, pp. 267-271 (Jun. 12, 2001).
Gim-Alldent Deutschland, "Das DUX System: Die Technik," 2 pages total (2002).
Gottleib et al., "JCO Interviews Dr. James A. McNamura, Jr., on the Frankel Appliance: Part 2: Clinical 1-1 Management," J. Clin. Orthod., 16(6):390-407 (Jun. 1982).
Grayson, "New Methods for Three Dimensional Analysis of Craniofacial Deformity, Symposium: JW Computerized Facial Imaging in Oral and Maxiiofacial Surgery," AAOMS, 3 pages total, (Sep. 13, 1990).
Guess et al., "Computer Treatment Estimates In Orthodontics and Orthognathic Surgery," JCO, pp. 262-28 (Apr. 1989).
Heaven et a/., "Computer-Based Image Analysis of Artificial Root Surface Caries," Abstracts of Papers, J. Dent. Res., 70:528 (Apr. 17-21, 1991).
Highbeam Research, "Simulating Stress Put on Jaw," Tooling & Production [online], Nov. 1996, n pp. 1-2, retrieved from the Internet on Nov. 5, 2004, URL http://static.highbeam.eom/t/toolingampproduction/november011996/simulatingstressputonfa . . . >.
Hikage, "Integrated Orthodontic Management System for Virtual Three-Dimensional Computer Graphic Simulation and Optical Video Image Database for Diagnosis and Treatment Planning", Journal of Japan KA Orthodontic Society, Feb. 1987, English translation, pp. 1-38, Japanese version, 46(2), pp. 248-269 (60 pages total).
Hoffmann, et al., "Role of Cephalometry for Planning of Jaw Orthopedics and Jaw Surgery Procedures," (Article Summary in English, article in German), Informatbnen, pp. 375-396 (Mar. 1991).
Hojjatie et al., "Three-Dimensional Finite Element Analysis of Glass-Ceramic Dental Crowns," J. Biomech., 23(11):1157-1166 (1990).
Huckins, "CAD-CAM Generated Mandibular Model Prototype from MRI Data," AAOMS, p. 96 (1999).
Important Tip About Wearing the Red White & Blue Active Clear Retainer System, Allesee Orthodontic Appliances-Pro Lab, 1 page 1998).
JCO Interviews, Craig Andreiko , DDS, MS on the Elan and Orthos Systems, JCO, pp. 459-468 (Aug. 1994).
JCO Interviews, Dr. Homer W. Phillips on Computers in Orthodontic Practice, Part 2, JCO. 1997; 1983:819-831.
Jerrold, "The Problem, Electronic Data Transmission and the Law," AJO-DO, pp. 478-479 (Apr. 1988).
Jones et al., "An Assessment of the Fit of a Parabolic Curve to Pre- and Post-Treatment Dental Arches," Br. J. Orthod., 16:85-93 (1989).
JP Faber et al., "Computerized Interactive Orthodontic Treatment Planning," Am. J. Orthod., 73(1):36-46 (Jan. 1978).
Kamada et.al., Case Reports On Tooth Positioners Using LTV Vinyl Silicone Rubber, J. Nihon University School of Dentistry (1984) 26(1): 11-29.
KAMADA et.al., Construction of Tooth Positioners with LTV Vinyl Silicone Rubber and Some Case KJ Reports, J. Nihon University School of Dentistry (1982) 24(1):1-27.
Kanazawa et al., "Three-Dimensional Measurements of the Occlusal Surfaces of Upper Molars in a Dutch Population," J. Dent Res., 63(11):1298-1301 (Nov. 1984).
Kesling, Coordinating the Predetermined Pattern and Tooth Positioner with Conventional Treatment, KN Am. J. Orthod. Oral Surg. (1946) 32:285-293.
Kesling et al., The Philosophy of the Tooth Positioning Appliance, American Journal of Orthodontics and Oral surgery. 1945; 31:297-304.
Kleeman et al., The Speed Positioner, J. Clin. Orthod. (1996) 30:673-680.

(56) References Cited

OTHER PUBLICATIONS

Kochanek, "Interpolating Splines with Local Tension, Continuity and Bias Control," Computer Graphics, ri 18(3):33-41 (Jul. 1984).
KM Oral Surgery (1945) 31 :297-30.
Kunii et al., "Articulation Simulation for an Intelligent Dental Care System," Displays 15:181-188 (1994).
Kuroda et al., Three-Dimensional Dental Cast Analyzing System Using Laser Scanning, Am. J. Orthod. Dentofac. Orthop. (1996) 110:365-369.
Laurendeau, et al., "A Computer-Vision Technique for the Acquisition and Processing of 3-D Profiles of 7 KR Dental Imprints: An Application in Orthodontics," IEEE Transactions on Medical Imaging, 10(3):453-461 (Sep. 1991).
Leinfelder, et al., "A New Method for Generating Ceramic Restorations: a CAD-CAM System," J. Am. 1-1 Dent. Assoc., 118(6):703-707 (Jun. 1989).
Manetti, et al., "Computer-Aided Cefalometry and New Mechanics in Orthodontics," (Article Summary in English, article in German), Fortschr Kieferorthop. 44, 370-376 (Nr. 5), 1983.
McCann, "Inside the ADA," J. Amer. Dent. Assoc., 118:286-294 (Mar. 1989).
McNamara et al., "Invisible Retainers," J. Cfin. Orthod., pp. 570-578 (Aug. 1985).
McNamara et al., Orthodontic and Orthopedic Treatment in the Mixed Dentition, Needham Press, pp. 347-353 (Jan. 1993).
Moermann et al., "Computer Machined Adhesive Porcelain Inlays: Margin Adaptation after Fatigue Stress," IADR Abstract 339, J. Dent. Res., 66(a):763 (1987).
Moles, "Correcting Mild Malalignments—As Easy As One, Two, Three," AOA/Pro Corner, vol. 11, No. 1, 2 pages (2002).
Mormann et al., "Marginale Adaptation von adhasuven Porzellaninlays in vitro," Separatdruck aus: Schweiz. Mschr. Zahnmed. 95: 1118-1129, 1985.
Nahoum, "The Vacuum Formed Dental Contour Appliance," N. Y. State Dent. J., 30(9):385-390 (Nov. 1964).
Nash, "CEREC CAD/CAM Inlays: Aesthetics and Durability in a Single Appointment," Dent. Today, 9(8):20, 22-23 (Oct. 1990).
Nishiyama et al., "A New Construction of Tooth Repositioner by LTV Vinyl Silicone Rubber," J. Nihon Univ. Sch. Dent., 19(2):93-102 (1977).
Paul et al., "Digital Documentation of Individual Human Jaw and Tooth Forms for Applications in Orthodontics, Oral Surgery and Forensic Medicine" Proc. of the 24th Annual Conf, of the IEEE Industrial Electronics Society (IECON '98), Sept. 4, 1998, pp. 2415-2418.
Pinkham, "Foolish Concept Propels Technology," Dentist, 3 pages total, Jan./Feb. 1989.
Pinkham, "Inventor's CAD/CAM May Transform Dentistry," Dentist, 3 pages total, Sep. 1990.
Ponitz, "Invisible Retainers," Am. J. Orthod., 59(3):266-272 (Mar. 1971).
Procera Research Projects, "Procera Research Projects 1993— Abstract Collection," pp. 3-7; 28 (1993).
Proffit et al., Contemporary Orthodontics, (Second Ed.), Chapter 15, Mosby Inc., pp. 470-533 (Oct. 1993).
Raintree Essix & ARS Materials, Inc., Raintree Essix, Technical Magazine Table of contents and Essix Appliances,< http:// www.essix.com/magazine/defaulthtml> Aug. 13, 1997.
Redmond et al., "Clinical Implications of Digital Orthodontics," Am. J. Orthod. Dentofacial Orthop., 117(2):240-242 (2000).
Rekow, "A Review of the Developments in Dental CAD/CAM Systems," (contains references to Japanese efforts and content of the papers of particular interest to the clinician are indicated with a one line summary of their content in the bibliography), Curr. Opin. Dent., 2:25-33 (Jun. 1992).
Rekow, "CAD/CAM in Dentistry: A Historical Perspective and View of the Future," J. Can. Dent. Assoc., 58(4):283, 287-288 (Apr. 1992).
Rekow, "Computer-Aided Design and Manufacturing in Dentistry: A Review of the State of the Art," J. Prosthet. Dent., 58(4):512-516 (Oct. 1987).
Rekow, "Dental CAD-CAM Systems: What is the State of the Art?", J. Amer. Dent. Assoc., 122:43-48 1991.
Rekow et al., "CAD/CAM for Dental Restorations—Some of the Curious Challenges," IEEE Trans. Biomed. Eng., 38(4):314-318 (Apr. 1991).
Rekow et al., "Comparison of Three Data Acquisition Techniques for 3-D Tooth Surface Mapping," Annual International Conference of the IEEE Engineering in Medicine and Biology Society, 13(1):344-345 1991.
Rekow, "Feasibility of an Automated System for Production of Dental Restorations, Ph.D. Thesis," Univ, of Minnesota, 244 pages total, Nov. 1988.
Richmond et al., "The Development of a 3D Cast Analysis System," Br. J. Orthod., 13(1):53-54 (Jan. 1986).
Richmond et al., "The Development of the PAR Index (Peer Assessment Rating): Reliability and Validity," Eur. J. Orthod., 14:125-139 (1992).
Richmond, "Recording The Dental Cast In Three Dimensions," Am. J. Orthod. Dentofacial Orthop., 92(3):199-206 (Sep. 1987).
Rudge, "Dental Arch Analysis: Arch Form, A Review of the Literature," Eur. J. Orthod., 3(4) :279-284 1981.
Sakuda et al., "Integrated Information-Processing System In Clinical Orthodontics: An Approach with Use of a Computer Network System," Am. J. Orthod. Dentofacial Orthop., 101(3): 210-220 (Mar. 1992).
Schellhas et al., "Three-Dimensional Computed Tomography in Maxillofacial Surgical Planning," Arch. Otolamp!. Head Neck Sur9., 114:438-442 (Apr. 1988).
Schroeder et al., Eds. The Visual Toolkit, Prentice Hall PTR, New Jersey (1998) Chapters 6, 8 & 9, (pp. 153-210, 309-354, and 355-428, respectively.
Shilliday, (1971). Minimizing finishing problems with the mini-positioner, Am. J. Orthod. 59:596-599.
Siemens, "CEREC—Computer-Reconstruction," High Tech in der Zahnmedizin, 14 pages total (2004).
Sinclair, "The Readers' Corner," J. Clin. Orthod., 26(6):369-372 (Jun. 1992).
Sirona Dental Systems GmbH, CEREC 3D, Manuel utiiisateur, Version 2.0X (in French), 2003,114 pages total.
Stoll et al., "Computer-aided Technologies in Dentistry," (article summary in English, article in German), Dtsch Zahna'rztl Z 45, pp. 314-322 (1990).
Sturman, "Interactive Keyframe Animation of 3-D Articulated Models," Proceedings Graphics Interface '84, May-Jun. 1984, pp. 35-40.
The Choice Is Clear: Red, White & Blue . . . The Simple, Affordable, No-Braces Treatment, Allesee HI Orthodontic Appliances-Pro Lab product information for doctors. http://ormco.com/aoa/appliancesservices/RWB/doctorhtml>, 5 pages (May 19, 2003).
The Choice is Clear: Red, White & Blue . . . The Simple, Affordable, No-Braces Treatment, Allesee HJ Orthodontic Appliances-Pro Lab product information for patients,< http://ormco.com/aoa/appliancesservices/RWB/patients.html>, 2 pages (May 19, 2003).
The Choice Is Clear: Red, White & Blue . . . The Simple, Affordable, No-Braces Treatment, Allesee Orthodontic Appliances-Pro Lab product information, 6 pages (2003).
The Red, White & Blue Way to Improve Your Smile! Allesee Orthodontic Appliances-Pro Lab product information for patients, 2 p. 1992.
Truax L., "Truax Clasp-Less(TM) Appliance System," Funct. Orthod., 9(5):22-4, 26-8 (Sep.-Oct. 1992).
Tru-Tain Orthodontic & Dental Supplies, Product Brochure, Rochester, Minnesota 55902, 16 pages total (1996).
U.S. Department of Commerce, National Technical Information Service, "Automated Crown Replication Using Solid Photography SM," Solid Photography Inc., Melville NY, Oct. 1977, 20 pages total.

(56) References Cited

OTHER PUBLICATIONS

U.S. Department of Commerce, National Technical Information Service, "Holodontography: An Introduction to Dental Laser Holography," School of Aerospace Medicine Brooks AFB Tex, Mar. 1973, 37 pages total.
U.S. Appl. No. 60/050,342, filed Jun. 20, 1997, 41 pages total.
Van Der Linden, "A New Method to Determine Tooth Positions and Dental Arch Dimensions," J. Dent. Res., 51(4):1104 (Jul.-Aug. 1972).
Van Der Linden et al., "Three-Dimensional Analysis of Dental Casts by Means of the Optocom," J. Dent. Res., p. 1100 (Jul.-Aug. 1972).
Van Der Zel, "Ceramic-Fused-to-Metal Restorations with a New CAD/CAM System," Quintessence Int., 24(11)769-778 (1993.
Varady et al., "Reverse Engineering Of Geometric Models—An Introduction," Computer-Aided Design, 29(4):255-268,1997.
Verstreken et al., "An Image-Guided Planning System for Endosseous Oral Implants," IEEE Trans. Med. Imaging, 17(5):842-852 (Oct. 1998).
Warunek et al., Physical and Mechanical Properties of Elastomers in Orthodonic Positioners, Am J. Orthod. Dentofac. Orthop, vol. 95, No. 5, (May 1989) pp. 399-400.
Warunek et.al., Clinical Use of Silicone Elastomer Applicances, JCO (1989) XXIII(10):694-700.
Wells, Application of the Positioner Appliance in Orthodontic Treatment, Am. J. Orthodont. (1970) 58:351-366.
Williams, "Dentistry and CAD/CAM: Another French Revolution," J. Dent. Practice Admin., pp. 2-5 (Jan./Mar. 1987).
Williams, "The Switzerland and Minnesota Developments in CAD/CAM," J. Dent. Practice Admin., pp. 50-55 (Apr./Jun. 1987.
Wishan, "New Advances in Personal Computer Applications for Cephalometric Analysis, Growth Prediction, Surgical Treatment Planning and Imaging Processing," Symposium: Computerized Facial Imaging in Oral and Maxiiofacial Surgery Presented on Sep. 13, 1990.
WSCG'98—Conference Program, "The Sixth International Conference in Central Europe on Computer Graphics and Visualization '98," Feb. 9-13, 1998, pp. 1-7, retrieved from the Interneton Nov. 5, 2004, URL<http://wscg.zcu.cz/wscg98/wscg98.h>.
Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001).
Yamamoto et al., "Optical Measurement of Dental Cast Profile and Application to Analysis of Three-Dimensional Tooth Movement in Orthodontics," Front. Med. Biol. Eng., 1(2):119-130 (1988).
Yamamoto et al., "Three-Dimensional Measurement of Dental Cast Profiles and Its Applications to Orthodontics," Conf. Proc. IEEE Eng. Med. Biol. Soc., 12(5):2051-2053 (1990).
Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.
Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980).
Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).
Yoshii, "Research on a New Orthodontic Appliance: The Dynamic Positioner (D.P.); III. The General Concept of the D.P. Method and Its Therapeutic Effect, Part 1, Dental and Functional Reversed Occlusion Case Reports," Nippon Dental Review, 457:146-164 (Nov. 1980).
Yoshii, "Research on a New Orthodontic Appliance: The Dynamic Positioner (D.P.); III.—The General Concept of the D.P. Method and Its Therapeutic Effect, Part 2. Skeletal Reversed Occlusion Case Reports," Nippon Dental Review, 458:112-129 (Dec. 1980).
You May Be A Candidate For This Invisible No-Braces Treatment, Allesee Orthodontic Appliances-Pro Lab product information for patients, 2 pages (2002).
International search report with written opinion dated Oct. 25, 2018 for PCT/US2018/040478.

\* cited by examiner

TREATMENT OF TEMPEROMANDIBULAR JOINT DYSFUNCTION WITH ALIGNER THERAPY

CROSS-REFERENCE

This application claims the benefit of U.S. Provisional Application No. 62/527,856, filed Jun. 30, 2017, which application is incorporated herein by reference.

BACKGROUND OF THE INVENTION

Temporomandibular joint dysfunction (TMD) is a dysfunction of the temporomandibular joints (TMJ) or the muscles of mastication. Significant amount of orofacial pain can result from TMD including headaches, earaches, jaw and neck pain, as well as abnormal opening and closing of the jaw. Options for managing TMD include an apparatus for modifying tooth contacts or condylar position, moving teeth, or surgery. Transparent shell appliances can be effective in alleviating or eliminating pain associated with TMJ. Transparent shell appliances can be custom designed for each patient. When designing the apparatus, the movement path is determined for the movement of one or more teeth from an initial arrangement to a target arrangement. A bite scan is obtained to determine the current jaw relation from which the desired jaw relation (e.g., an ideal jaw relation) can be calculated. For example, in some cases a desired jaw relation can be a centric relation, corresponding to a clinically repeatable positioning of the condyle in the mandibular fossa. Orthodontic treatment without considering desired jaw relation may constrain the condylar position or cause unhealthy muscle activations, which could cause or contribute to TMD. An appliance which performs orthodontic movement to a desired jaw relation may prevent unhealthy habitual muscle activations could help alleviate or prevent TMD.

SUMMARY

The methods and apparatus disclosed herein provide improved movement of teeth and jaws useful for the treatment and/or prevention of TMD. In many aspects, a method of treating and/or preventing TMD is provided. First and second bite scan data of a dentition of a patient are obtained. The first bite scan data are obtained with the patient's jaws in a target bite configuration, and the second bite scan data are obtained with the patient's jaws in a natural bite configuration. Based on the first and second bite scan data, a plurality of appliances is designed. The appliances are configured to apply tooth-moving and jaw-moving forces to the patient's dentition so as to move the patient's dentition from the natural bite configuration to a final bite configuration. The final bite configuration corresponds to the target bite configuration. The plurality of appliances is configured to move the dentition of the patient through a sequence on incremental steps when the plurality of appliances is worn in succession, thereby moving the dentition to the final bite configuration. Designing the plurality of appliances includes determining one or more gaps between upper teeth of the dentition and lower teeth of the dentition present during at least one of the incremental steps. At least one of said plurality of appliances comprises one or more occlusal surface features positioned to fill the one or more gaps when the appliance is worn by the patient. One or more of the plurality of appliances is designed to apply tooth moving forces to close said one or more gaps.

The one or more gaps can include one or more occlusal gaps, for instance.

In some aspects, obtaining first bite scan data comprises scanning the dentition of the patient in the target bite configuration and obtaining second bite scan data comprises scanning the dentition of the patient in the natural bite configuration.

The method can include manufacturing the plurality of appliances. The method can additionally or alternatively include providing the plurality of appliances to the patient. In some cases, the method includes placing at least one of the plurality of appliances on the dentition of the patient.

In some aspects, each of the plurality of appliances comprises a polymeric shell. In some cases, each of the plurality of appliances comprises a first polymeric shell shaped to receive upper teeth of the dentition and a second polymeric shell shaped to receive lower teeth of the dentition.

In some aspects, the final bite configuration comprises a jaw position corresponding to the target bite configuration and positions of one or more teeth of the final bite configuration are changed relative to the target bite configuration. In some cases, the positions of the one or more teeth of the final bite configuration are changed to avoid one or more lower-to-upper teeth collisions present in the target bite configuration. In some aspects, each incremental step in said sequence of incremental steps comprises tooth contact paths for each of a plurality of teeth, and wherein designing said plurality of appliances comprises optimizing the tooth contact paths for said incremental steps to avoid tooth collisions during said incremental steps.

In some aspects, at least one of the plurality of appliances is a removable appliance. For instance, each of the plurality of appliances can be a removable appliance.

In many aspects, an appliance for the treatment or prevention of TMD is provided. The appliance a shell comprising a plurality of tooth-receiving cavities shaped to fit teeth of a first arch of a patient's dentition. The appliance also comprises an occlusal repositioning splint. The occlusal repositioning splint comprises a first surface shaped to attach to the shell and extend over a plurality of tooth-receiving cavities of the shell and a second surface opposite the first surface and having a varying surface height. The second surface presents an adjusted occlusal surface to teeth of second arch of the patient's dentition when the appliance is worn. The adjusted occlusal surface is shaped to alter the natural occlusion of the first and second arches, thereby urging the patient's bite from a natural bite configuration to a target bite configuration. The occlusal repositioning splint is shaped to fill a gap between occlusal surfaces of the teeth of the first and second arch resulting from the target bite configuration.

In some aspects, the appliance further comprises a tooth engagement structure to apply a tooth moving force when the appliance is worn, thereby urging one or more teeth of the patient to fill the gap between occlusal surfaces. In some aspects, the adjusted occlusal surface can be shaped to occlude with an appliance shell worn on the teeth of the second arch of the patient's dentition.

In some cases, the occlusal repositioning splint is removably attached to the shell; in some cases the occlusal repositioning splint is integrally attached to the shell.

The second surface can be shaped to fit provide a disocclusion of posterior teeth in a resting jaw position. Alternatively or additionally, the second surface can comprise one or more sliding ramped contacts on anterior teeth of the patient. The sliding ramped contacts can be shaped to provide anterior guidance during lateral excursions and anterior protrusions of the jaw.

In some aspects, a plurality of appliances can be provided, including the appliance for the treatment or prevention of TMD. The plurality of appliances is configured to move the patient's dentition from the natural bite configuration to a final bite configuration through a sequence on incremental steps when the plurality of appliances is worn in succession. In some cases, at least one appliance of the plurality of appliances comprises a tooth engagement structure to apply a tooth moving force when the appliance is worn, thereby urging one or more teeth of the patient to fill the gap between occlusal surfaces. The at least one appliance can be the same appliance as the appliance for the treatment of TMD, or it can be a different appliance. In some cases, each of the plurality of appliances is an appliance for the treatment or prevention of TMD.

In many aspects, an appliance for the treatment or prevention of TMD is provided. The appliance comprises a shell comprising a plurality of tooth-receiving cavities shaped to fit teeth of a first arch of a patient's dentition and a lingual repositioning splint attached to the shell, and extending away from the shell. The lingual repositioning splint comprises a surface shaped to contact one or more teeth of a second arch of the patient when the appliance is worn, and to thereby adjust the patient's bite from a natural bite configuration toward a target bite configuration based on the contact between the one or more teeth of the second arch and the surface of the lingual repositioning splint.

In some aspects, the surface is shaped with an indentation to receive the one or more teeth of the second arch. The indentation is positioned to provide an incremental adjustment of the bite of the patient away from the natural bite configuration and toward the target bite configuration. In some cases, the surface is shaped to correct an overbite; in some cases, the surface is shaped to correct an underbite. The appliance can further comprise a tooth engagement structure to apply a tooth moving force when the appliance is worn.

In many aspects, a system for treating and/or preventing temporomandibular joint dysfunction (TMD) is provided. The system comprises a processor and memory storing instructions that, when executed, perform a method. The method comprises receiving first and second bite scan data of a dentition of a patient. The first scan data are with the patient's jaws in a target bite configuration; the second scan data are with the patient's jaws in a natural bite configuration. The method further comprises designing a plurality of appliances based on the first and second bite scan data. The plurality of appliances are configured to apply tooth-moving and jaw-moving forces to the patient's dentition so as to move the patient's dentition from the natural bite configuration to a final bite configuration corresponding to the target bite configuration through a sequence on incremental steps when the plurality of appliances is worn in succession. Designing the plurality of appliances includes determining one or more occlusal gaps between upper teeth of the dentition and lower teeth of the dentition present during at least one of the incremental steps. At least one of the plurality of appliances comprises one or more occlusal surface features positioned to fill the one or more occlusal gaps when the appliance is worn by the patient, and one or more of the plurality of appliances is designed to apply tooth moving forces to close said one or more occlusal gaps.

In some aspects, the system is further configured to generate instructions for manufacturing said plurality of appliances. In some aspects, each of the plurality of appliances comprises a polymeric shell. In some aspects, each of the plurality of appliances comprises a first polymeric shell shaped to receive upper teeth of the dentition and a second polymeric shell shaped to receive lower teeth of the dentition.

In some aspects, the final bite configuration comprises a jaw position corresponding to the target bite configuration and wherein positions of one or more teeth of the final bite configuration are changed relative to the target bite configuration. In some cases, the positions of the one or more teeth of the final bite configuration are changed to avoid one or more lower-to-upper teeth collisions present in the target bite configuration.

In some aspects, at least one of the plurality of appliances is a removable appliance. In some cases, each of the plurality of appliances is a removable appliance.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present disclosure will be obtained by reference to the following detailed description that sets forth illustrative embodiments, in which the principles of the invention are utilized, and the accompanying drawings of which:

DETAILED DESCRIPTION

Figure 1:
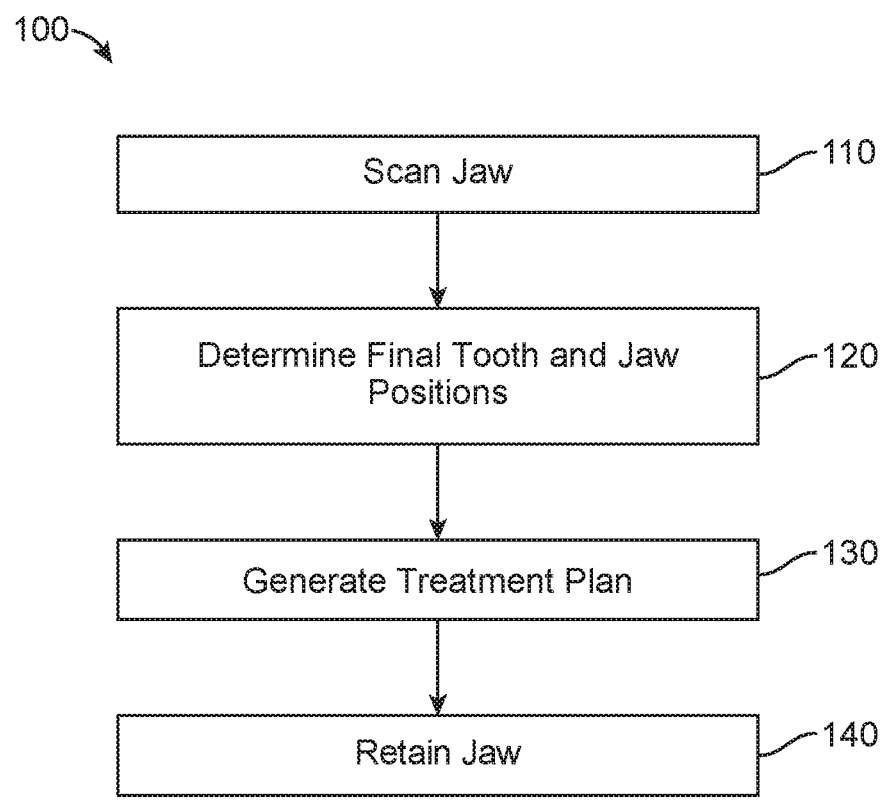
FIG. 1 illustrates a method of treating TMD comprising obtaining a scan at the desired jaw position, determining the final position (FiPos) at the desired position, determining the tooth path and intermediate stages, and continuing therapy, in accordance with embodiments.

In many embodiments, a method of moving a tooth of a patient from a first position and orientation to a second position and orientation is provided. The method comprises providing a polymeric shell appliance shaped to fit a plurality of teeth. The polymeric shell appliance comprises one or more teeth receiving cavities to couple the tooth to one or more other teeth of the plurality with one or more other tooth receiving cavities. The polymeric shell appliance applies a force to the tooth and moves the tooth from the first position and orientation to the second position and orientation. The polymeric shell appliance can comprise a repositioning splint that can be used to adjust bite equilibrium.

In many embodiments, a method is provided for moving a tooth of a patient from a first position and orientation to a second position and orientation. A plurality of orthodontic appliances shaped to fit a plurality of teeth in succession is provided. Each of the plurality of orthodontic appliances comprises a repositioning splint sized to extend along the surface of the teeth used for mastication in order to couple the tooth to one or more other teeth of the plurality. A location of the repositioning splint relative to the one or more teeth receiving the splint varies among the plurality of orthodontic appliances in order to create bite equilibrium while the tooth moves from the first position and orientation to the second position and orientation.

In many embodiments, method of manufacturing a plurality of orthodontic appliance shaped to fit a plurality of teeth in succession is provided. A movement path is determined to move the one or more teeth from an initial arrangement to a target arrangement. A force system to produce movement of the one or more teeth along the movement path is determined. An appliance geometry is determined for an orthodontic appliance configured to produce the force system. The orthodontic appliance is directly fabricated based on the determined appliance geometry.

Treatment Plan

The configuration of the orthodontic appliances herein can be determined according to a treatment plan for a patient, e.g., a treatment plan involving successive administration of a plurality of appliances for incrementally repositioning teeth and the jaw. Computer-based treatment planning and/or appliance manufacturing methods can be used in order to facilitate the design and fabrication of appliances. For instance, one or more of the appliance components described herein can be digitally designed and fabricated with the aid of computer-controlled manufacturing devices (e.g., computer numerical control (CNC) milling, computer-controlled rapid prototyping such as 3D printing, etc.). The computer-based methods presented herein can improve the accuracy, flexibility, and convenience of appliance fabrication.

Automatic Diagnosis of TMD

TMD can be diagnosed in a patient by examining the patient's jaw position during regular lower jaw movement. Natural lower jaw movements can be captured by three dimensional scans of the lower and upper jaw. Multiple scans, such as x-rays, can be acquired of a sequential positions during the movement of the lower jaw. For example, scans of the patient's jaw in an initial bite location, a desired bite position, and the jaw and various positions for recording the articulation of the patient's jaw and to aid in predicting articulation in a final TMD corrected jaw position. The trajectory of complete jaw movement can be determined based on the multiple scanned positions. The trajectory of the patient's jaw movement may be compared to an ideal healthy trajectory of lower jaw movement. During the comparison, qualitative and quantitative discrepancies can be determined based on the trajectory of jaw movement between the patient and the healthy individual.

Qualitative and quantitative discrepancies may include an evaluation of the engaged from the occlusal surfaces of the teeth of the jaws and the position of each tooth of the lower jaw relative to the position of each tooth in the fixed upper jaw. The trajectory of complete jaw movement of the patient can be determined from the multiple scans using an intraoral scan, such as by using an iTero intraoral scanner, and software post-processing methods. TMD can be diagnosed from examining the trajectory of complete jaw movement as displayed in the multiple scans and comparing this trajectory to a healthy trajectory of lower jaw movement, such as that of a healthy individual or an articulator that simulates healthy trajectory.

Automatic Verification of the Final Position of Treatment

The final position of teeth can be also pre-determined from the trajectory of complete jaw movement. The final positions of the teeth can be determined based on an ideal healthy trajectory of lower jaw movement. The pre-determined final positions of the teeth can be for an individual with TMD. Natural lower jaw movements of the patient can be captured by three dimensional scans of the lower and upper jaw. Multiple scans can be acquired of the sequential positions during the movement of the lower jaw. The trajectory of complete jaw movement can be determined based on scans at multiple positions. The trajectory of the patient's jaw movement is compared to the trajectory of healthy lower jaw movement. The trajectory of complete jaw movement can be verified by reviewing the final position of the teeth. The final position of the teeth in the treatment plan can be verified so that lower-to-upper teeth collision is absent with respect to the natural movement of the jaw. The final position can be modified to eliminate possible collisions. The final position of the teeth can also be verified so that canine guidance is present in the final position of the teeth with respect to the natural movement of the jaw. The final positions of the teeth with respect to the natural movement of the jaw can be determined and verified using the trajectory of complete jaw movement of the patient can be determined and reviewed from the multiple scans using iTero and software post-processing methods.

Automatic Treatment Plan for the Desired Jaw Relation

The treatment plan can consist of a pre-determined trajectory of complete jaw movement. Natural lower jaw movements can be captured by three dimensional scans of the lower and upper jaw. Multiple scans can be acquired of the sequential positions during the movement of the lower jaw. The scan can estimate the neutral position of the lower jaw. The scan can estimate the jaw position of lowest muscle tension. The input from the patient, such as the patient's feedback regarding neutral or lowest muscle tension, can be recorded at the time of scanning. Machine learning can be applied to predict the neutral positions for new cases after the input has been recorded from multiple patients. The treatment plan can consist of an established final position of the occlusion or the closed jaw corresponding to the neutral position of the jaw.

The staging in the treatment plan can be verified for significant deviations of the intermediate bite from the neutral position. The staging can be modified to eliminate significant deviations of the intermediate bite from the neutral position.

Plurality of Devices

TMD may be treated with a treatment plan involving successive administration of a plurality of appliances for incrementally repositioning teeth. As illustrated in FIG. 1, the treatment plan 100 may comprise scanning a dentition of a patient to obtain a first bite scan. The bite scan can be at a desired jaw position 110. The bite scan can be of a patient's jaws in a natural bite configuration. The final position can be determined according to step 120. The path of dentition movement between the natural jaw position and the desired jaw position can be segmented into intermediate stages 130. A plurality of devices is configured to apply tooth-moving and jaw-moving forces to the patient's dentition so as to move the patient's dentition from the natural bite configuration to a final bite configuration. The movement corresponds to the target bite configuration through a sequence of incremental steps. The final device in the plurality of devices can be at the final desired jaw position. Once the dentition reaches the final jaw position, the final device can also serve to retain final jaw position 140.

Figure 4:
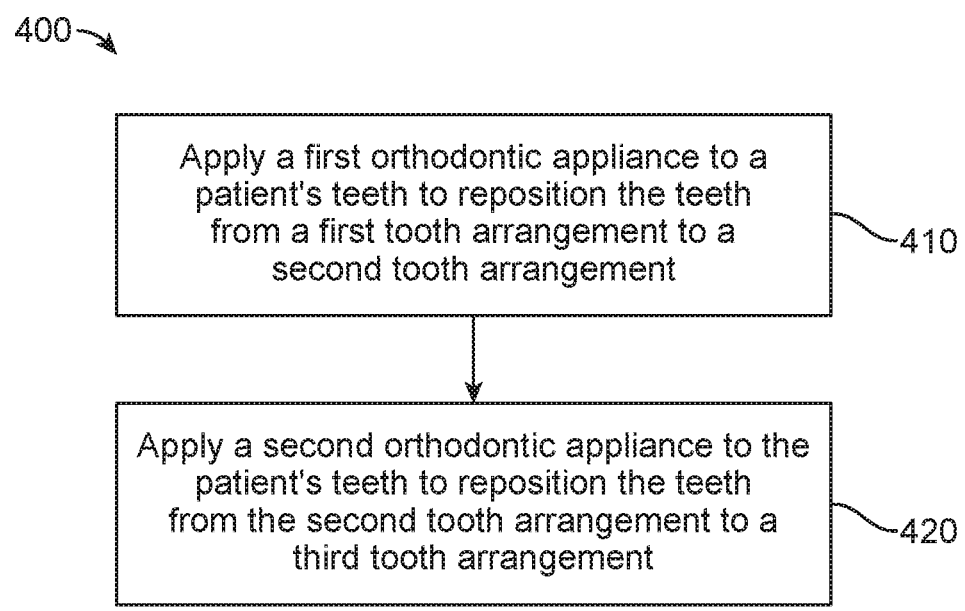
FIG. 4 illustrates a method of orthodontic treatment using a plurality of appliances, in accordance with embodiments.
Figure 5:
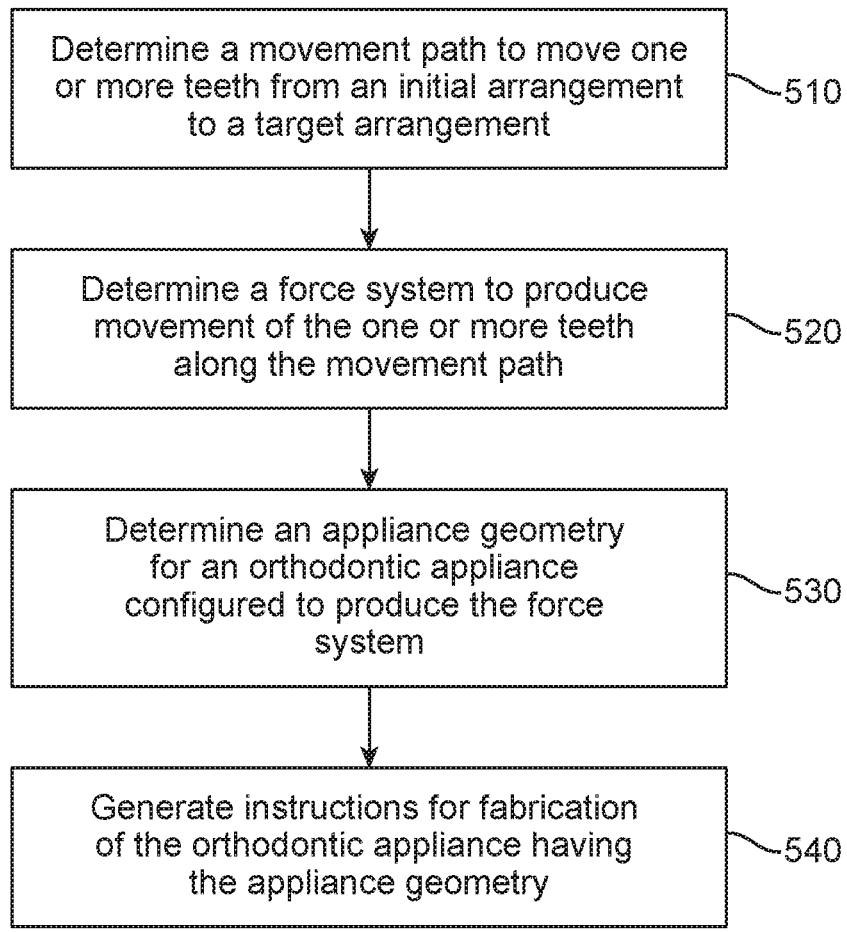
FIG. 5 illustrates a method for designing an orthodontic appliance, in accordance with embodiments

FIG. 4 illustrates a method 400 of orthodontic treatment using a plurality of appliances, in accordance with embodiments. The method 400 can be practiced using any of the appliances or appliance sets described herein. In step 410, a first orthodontic appliance is applied to a patient's teeth in order to reposition the teeth from a first tooth arrangement to a second tooth arrangement. In step 420, a second orthodontic appliance is applied to the patient's teeth in order to reposition the teeth from the second tooth arrangement to a third tooth arrangement. The method 400 can be repeated as necessary using any suitable number and combination of sequential appliances in order to incrementally reposition the patient's teeth from an initial arrangement to a target arrangement. The appliances can be generated all at the same stage or in sets or batches (e.g., at the beginning of a stage of the treatment), or the appliances can be fabricated one at a time, and the patient can wear each appliance until the pressure of each appliance on the teeth can no longer be felt or until the maximum amount of expressed tooth movement for that given stage has been achieved. A plurality of different appliances (e.g., a set) can be designed and even fabricated prior to the patient wearing any appliance of the plurality. After wearing an appliance for an appropriate period of time, the patient can replace the current appliance with the next appliance in the series until no more appliances remain. The appliances are generally not affixed to the teeth and the patient may place and replace the appliances at any time during the procedure (e.g., patient-removable appliances). The final appliance or several appliances in the series may have a geometry or geometries selected to overcorrect the tooth arrangement. For instance, one or more appliances may have a geometry that would (if fully achieved) move individual teeth beyond the tooth arrangement that has been selected as the "final." Such over-correction may be desirable in order to offset potential relapse after the repositioning method has been terminated (e.g., permit movement of individual teeth back toward their pre-corrected positions). Over-correction may also be beneficial to speed the rate of correction (e.g., an appliance with a geometry that is positioned beyond a desired intermediate or final position may shift the individual teeth toward the position at a greater rate). In such cases, the use of an appliance can be terminated before the teeth reach the positions defined by the appliance. Furthermore, over-correction may be deliberately applied in order to compensate for any inaccuracies or limitations of the appliance.

Data Processing System

Figure 2:
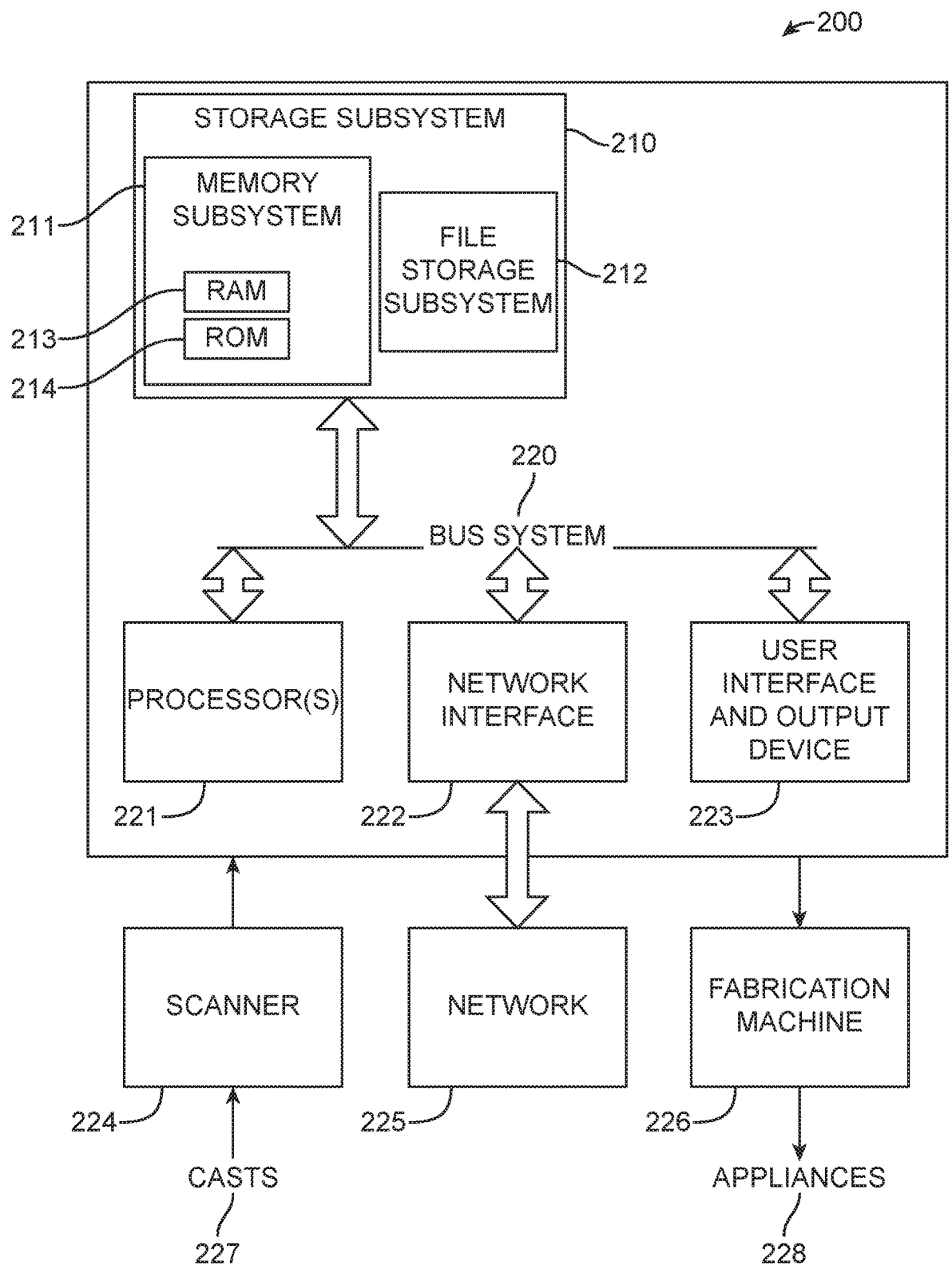
FIG. 2 is a simplified block diagram of a data processing system, in accordance with embodiments.

Data processing system 200, as illustrated in FIG. 2 in a simplified block diagram, may be used in executing methods and processes described herein. Data processing system 200 typically includes at least one processor 210 that communicates with one or more peripheral devices via bus subsystem 220. These peripheral devices typically include storage subsystem 210 (memory subsystem 211 and file storage subsystem 212), a set of user interface input and output devices 223, and an interface to outside networks 222. This interface is shown schematically as "Network Interface" block 222, and is coupled to corresponding interface devices in other data processing systems via communication network interface 225. Data processing system 200 can include, for example, one or more computers, such as a personal computer, workstation, mainframe, laptop, and the like.

The user interface input devices 223 are not limited to any particular device, and can typically include, for example, a keyboard, pointing device, mouse, scanner, interactive displays, touchpad, joysticks, etc. Similarly, various user interface output devices can be employed in a system of the invention, and can include, for example, one or more of a printer, display (e.g., visual, non-visual) system/subsystem, controller, projection device, audio output, and the like.

Storage subsystem 210 maintains the basic required programming, including computer readable media having instructions (e.g., operating instructions, etc.), and data constructs. The program modules discussed herein are typically stored in the storage subsystem 210. Storage subsystem 210 typically includes memory subsystem 211 and file storage subsystem 212. Memory subsystem 211 typically includes a number of memories (e.g., RAM 410, ROM 412, etc.) including computer readable memory for storage of fixed instructions, instructions and data during program execution, basic input/output system, etc. File storage subsystem 212 provides persistent (nonvolatile) storage for program and data files and can include one or more removable or fixed drives or media, hard disk, floppy disk, CD-ROM, DVD, optical drives, flash drives, and the like. One or more of the storage systems, drives, etc., may be located at a remote location, and therefore, coupled via a server on a network or via the internet or the World Wide Web. For example, the one or more storage systems can include distributed online storage such as cloud storage. In this context, the term "bus subsystem" is used generically so as to include any mechanism for letting the various components and subsystems communicate with each other as intended and can include a variety of suitable components or systems that would be known or recognized as suitable for use therein. It will be recognized that various components of the system can be, but need not necessarily be at the same physical location, but could be connected via various local-area or wide-area network media, transmission systems, etc.

Scanner 224 includes any means for obtaining a digital representation (e.g., images, surface topography data, etc.) of a patient's teeth (e.g., by scanning physical models of the teeth such as casts 227, by scanning impressions taken of the teeth, or by directly scanning the intraoral cavity), which can be obtained either from the patient or from a professional, such as an orthodontist, and includes means for providing the digital representation to data processing system 200 for further processing. Examples of suitable scanners include x-ray, optical, topographic, and ultrasound scanners, as well as tomographic scanners such as Cone Beam Computed Tomography (CBCT) scanners. Scanner 224 may be located at a location remote with respect to other components of the system and can communicate image data and/or information to the data processing system 200, for example, via a network interface 225. Fabrication system 226 fabricates appliances 228 based on a treatment plan, including data set information received from data processing system 200. Fabrication machine 226 can, for example, be located at a remote location and receive data set information from data processing system 200 via network interface 225.

The data processing aspects of the methods described herein can be implemented in digital electronic circuitry, or in computer hardware, firmware, software, or suitable combinations thereof. Data processing apparatus can be implemented in a computer program product tangibly embodied in a machine-readable storage device for execution by a programmable processor. Data processing steps can be performed by a programmable processor executing program instructions to perform functions by operating on input data and generating output. The data processing aspects can be implemented in one or more computer programs that are executable on a programmable system, the system including one or more programmable processors operably coupled to a data storage system. Generally, a processor will receive instructions and data from a read-only memory and/or a random access memory. Storage devices suitable for tangibly embodying computer program instructions and data include all forms of nonvolatile memory, such as: semiconductor memory devices, such as EPROM, EEPROM, and flash memory devices; magnetic disks such as internal hard disks and removable disks; magneto-optical disks; and CD-ROM disks.

Tooth Movement Pathway

In step 510, a movement path to move one or more teeth from an initial arrangement to a target arrangement is determined. The initial arrangement can be determined from a mold or a scan of the patient's teeth or mouth tissue, e.g., using wax bites, direct contact scanning, x-ray imaging, tomographic imaging, sonographic imaging, and other techniques for obtaining information about the position and structure of the teeth, jaws, gums and other orthodontically relevant tissue. From the obtained data, a digital data set can be derived that represents the initial (e.g., pretreatment) arrangement of the patient's teeth and other tissues. Optionally, the initial digital data set is processed to segment the tissue constituents from each other. For example, data structures that digitally represent individual tooth crowns can be produced. Advantageously, digital models of entire teeth can be produced, including measured or extrapolated hidden surfaces and root structures, as well as surrounding bone and soft tissue.

The target arrangement of the teeth (e.g., a desired and intended end result of orthodontic treatment) can be received from a clinician in the form of a prescription, can be calculated from basic orthodontic principles, and/or can be extrapolated computationally from a clinical prescription. With a specification of the desired final positions of the teeth and a digital representation of the teeth themselves, the final position and surface geometry of each tooth can be specified to form a complete model of the tooth arrangement at the desired end of treatment.

With both an initial position and a target position for each tooth, a movement path can be defined for the motion of each tooth. In some embodiments, the movement paths are configured to move the teeth in the quickest fashion with the least amount of round-tripping to bring the teeth from their initial positions to their desired target positions. The tooth paths can optionally be segmented, and the segments can be calculated so that each tooth's motion within a segment stays within threshold limits of linear and rotational translation. In this way, the end points of each path segment can constitute a clinically viable repositioning, and the aggregate of segment end points can constitute a clinically viable sequence of tooth positions. These teeth positions can be adjusted using dynamic bite information reflecting occlusion and interactions of teeth when the patient bites, so that moving from one point to the next in the sequence does not result in a collision of teeth.

In step 520, a force system to produce movement of the one or more teeth along the movement path is determined. A force system can include one or more forces and/or one or more torques. Different force systems can result in different types of tooth movement, such as tipping, translation, rotation, extrusion, intrusion, root movement, etc. Biomechanical principles, modeling techniques, force calculation/measurement techniques, and the like, including knowledge and approaches commonly used in orthodontia, may be used to determine the appropriate force system to be applied to the tooth to accomplish the tooth movement. In determining the force system to be applied, sources may be considered including literature, force systems determined by experimentation or virtual modeling, computer-based modeling, clinical experience, minimization of unwanted forces, etc.

In step 530, an appliance geometry for an orthodontic appliance configured to produce the force system is determined. The geometry may comprise one or more tooth engagement structures, and the tooth engagement structures may be configured to engage the surface of at least one tooth. The tooth surface chosen from engagement may be an interproximal surface, a buccal or lingual surface, an occlusal surface, or any other surface of the tooth, depending on the characteristics of the force on the tooth it is to elicit. The geometry may also comprise a specification of material as a function of location within the orthodontic appliance, for example, specifying certain portions to comprise elastic polymeric material and other portions to comprise rigid polymeric material.

Determination of the appliance geometry, material composition, and/or properties can be performed using a treatment or force application simulation environment. A simulation environment can include, e.g., computer modeling systems, biomechanical systems or apparatus, and the like. Optionally, digital models of the appliance and/or teeth can be produced, such as finite element models. The finite element models can be created using computer program application software available from a variety of vendors. For creating solid geometry models, computer aided engineering (CAE) or computer aided design (CAD) programs can be used, such as the AutoCAD® software products available from Autodesk, Inc., of San Rafael, Calif. For creating finite element models and analyzing them, program products from a number of vendors can be used, including finite element analysis packages from ANSYS, Inc., of Canonsburg, Pa., and SIMULIA(Abaqus) software products from Dassault Systèmes of Waltham, Mass.

Optionally, one or more appliance geometries can be selected for testing or force modeling. As noted above, a desired tooth movement, as well as a force system required or desired for eliciting the desired tooth movement, can be identified. Using the simulation environment, a candidate appliance geometry can be analyzed or modeled for determination of an actual force system resulting from use of the candidate appliance. One or more modifications can optionally be made to a candidate appliance, and force modeling can be further analyzed as described, e.g., in order to iteratively determine an appliance design that produces the desired force system.

In step 540, instructions for fabrication of the orthodontic appliance having the appliance geometry are generated. The instructions can be configured to control a fabrication system or device in order to produce the orthodontic appliance with the specified appliance geometry. In some embodiments, the instructions are configured for manufacturing the orthodontic appliance using direct fabrication (e.g., stereolithography, selective laser sintering, fused deposition modeling, 3D printing, continuous direct fabrication, multi-material direct fabrication, etc.), in accordance with the various methods presented herein. In alternative embodiments, the instructions can be configured for indirect fabrication of the appliance, e.g., by thermoforming.

Although the above steps show a method 500 of designing an orthodontic appliance in accordance with some embodiments, a person of ordinary skill in the art will recognize some variations based on the teaching described herein. Some of the steps may comprise sub-steps. Some of the steps may be repeated as often as desired. One or more steps of the method 500 may be performed with any suitable fabrication system or device, such as the embodiments described herein. Some of the steps may be optional, and the order of the steps can be varied as desired.

Bite Equilibrium During Tooth Movement

The "arch" is one of two dental arches in humans and many other species. The upper arch is also known as the maxillary arch or the superior arch. The lower arch is also known as the mandibular arch or the inferior arch. When the jaw closes, the dental arches approach each other and the mouth occludes or closes.

The "corresponding engagement surface" of the one or more teeth in the opposing arch is the occlusal surface of one or more teeth in the opposing arch as determined by the natural closing of the jaw.

The "natural closing of the jaw" is the closing of the jaw wherein the least effort is exerted to move the jaw to a closed position.

The "bite equilibrium" is a state of zero or minimal forces applied on the jaw after the natural closing of the jaw.

In many embodiments, a method of moving teeth of a patient from first positions and orientations to second positions and orientations is provided. The method comprises successively providing a plurality of orthodontic appliances shaped to fit a plurality of teeth. In some embodiments, for each of the plurality of appliances the one or more teeth receiving structures comprises one or more teeth receiving cavities.

Figure 3:
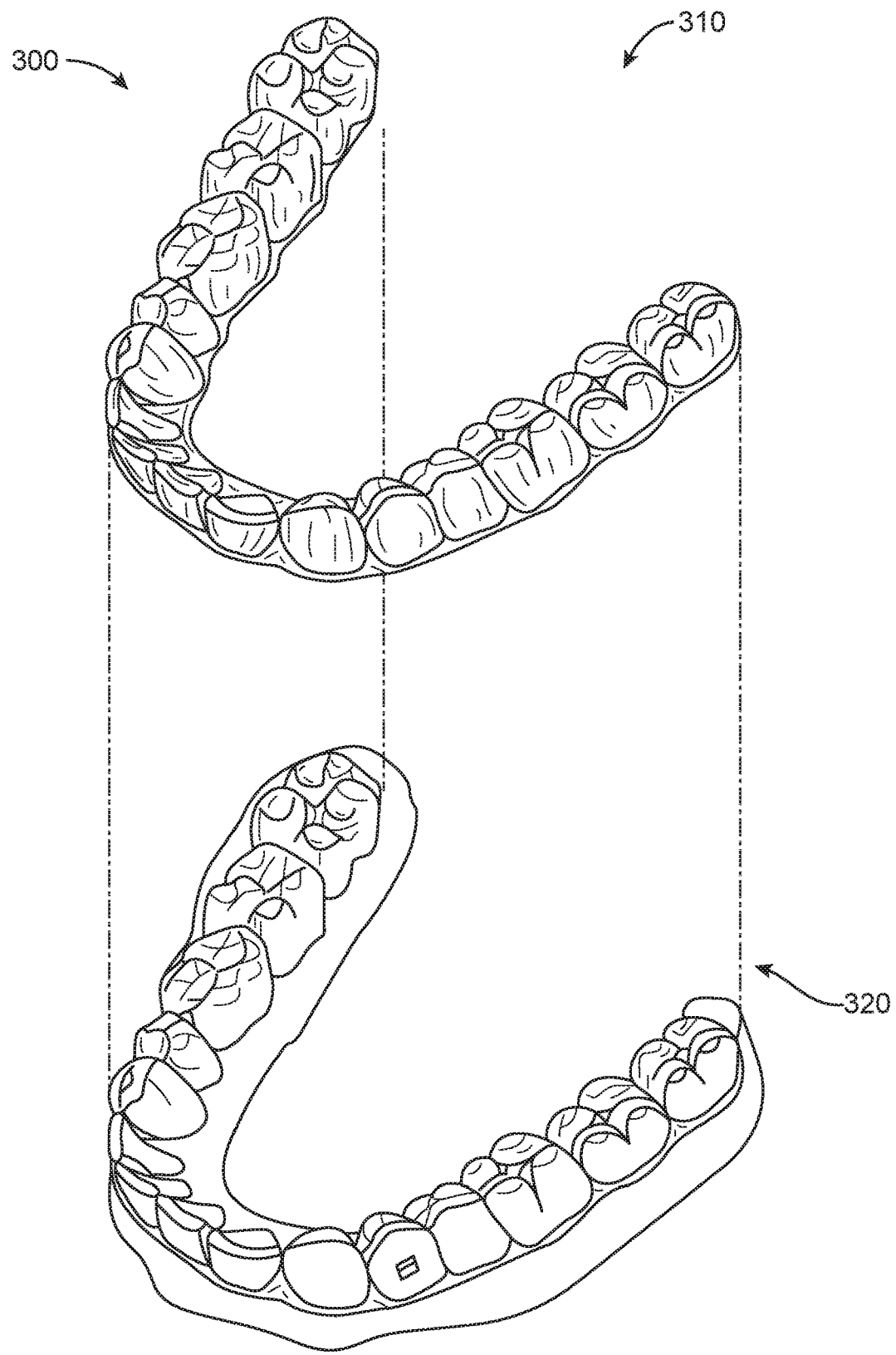
FIG. 3 illustrates a tooth repositioning system, in accordance with embodiments.

An orthodontic shell appliance shaped to fit a plurality of teeth is provided. As illustrated in FIG. 3, the shell appliance comprises an outer wall extending over buccal and lingual surfaces of the plurality of teeth. In some embodiments, the wall is shaped to receive one or more teeth and wherein the wall engages the one or more teeth with force in order to move the one or more teeth in response to forces.

In some embodiments, the outer surface of the outer wall comprises a buccal surface of the appliance; in some embodiments, the outer surface of the outer wall comprises a lingual surface of the appliance.

Repositioning Splint

In many embodiments, a method of moving teeth of a patient from first positions and orientations to second positions and orientations is provided. The method comprises successively providing a plurality of orthodontic appliances shaped to fit a plurality of teeth.

In some embodiments, for each of the plurality of appliances the one or more teeth receiving structures is coupled to a repositioning splint.

In some embodiments, for each of the plurality of appliances the one or more teeth receiving structures is coupled to an occlusal repositioning splint extending along the occlusal surface of the one or more tooth receiving structures.

In some embodiments, for each of the plurality of appliances the one or more teeth receiving structures is coupled to a lingual repositioning splint extending along the lingual surface of the one or more tooth receiving structures.

In many embodiments, a method of moving teeth of patient from first positions and orientations to second positions and orientations is provided. The method comprises successively providing a plurality of orthodontic appliances shaped to fit a plurality of teeth. For each of the plurality of appliances the one or more teeth receiving structures is coupled to a repositioning splint extending along the outer occlusal surface or lingual surface of the one or more tooth receiving structures. The plurality of appliances can result in a plurality of movements of the teeth from the first positions and orientations to the second positions and orientations when the plurality of appliances is worn in succession.

In many embodiments, a method of moving teeth of a patient from first positions and orientations to second positions and orientations is provided. The method comprises successively providing a plurality of orthodontic appliances shaped to fit a plurality of teeth. For each of the plurality of appliances the one or more teeth receiving structures is coupled to an occlusal repositioning splint, which is a repositioning splint extending along the occlusal surface of the one or more tooth receiving structures. In some embodiments, the occlusal repositioning splint contours the outer surface of the tooth receiving structure. Upon natural closing of the jaw, each of the plurality of occlusal repositioning splints can engage with the corresponding engagement occlusal surface. Each of the plurality of repositioning splints can conform to one or more teeth in the opposing arch. Upon the natural closing of the jaw, each of the plurality of occlusal repositioning splints can enable bite equilibrium, as well as adjusting bite position to relieve symptoms associated with TMD such as muscle strain.

In many embodiments, a method of moving teeth of a patient from first positions and orientations to second positions and orientations is provided. The method comprises successively providing a plurality of orthodontic appliances shaped to fit a plurality of teeth. For each of the plurality of appliances the one or more teeth receiving structures is coupled to a lingual repositioning splint, which is a repositioning splint extending along the lingual surface of the one or more tooth receiving structures. In some embodiments, the lingual repositioning splint contours the outer surface of the tooth receiving structure. Upon natural closing of the jaw, each of the plurality of lingual repositioning splints can engage with the corresponding engagement lingual surface. Each of the plurality of lingual repositioning splints can conform to one or more teeth in the opposing arch. Upon the natural closing of the jaw, each of the plurality of repositioning splints can enable bite equilibrium.

Occlusal Repositioning Splint

Figure 6A:
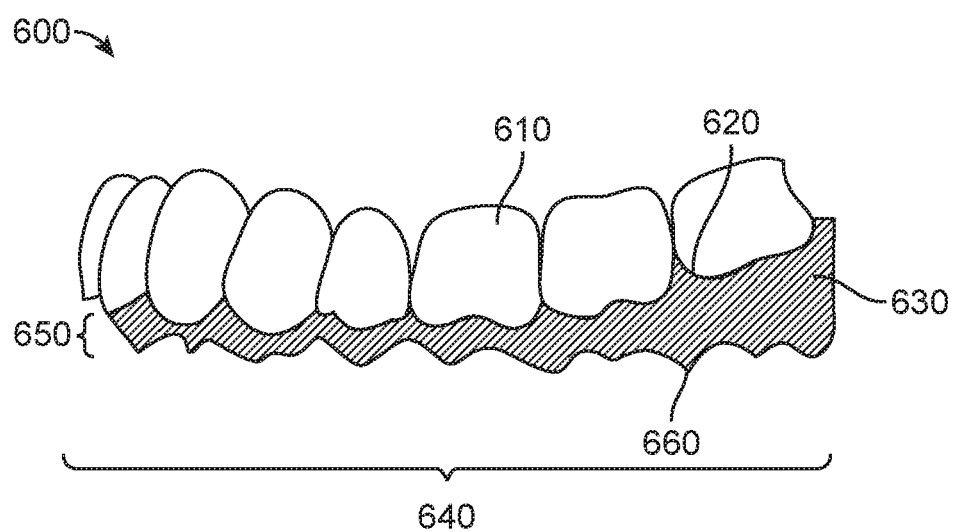
FIG. 6A illustrates an occlusal repositioning splint located on an occlusal surfaces of the dental structure, in accordance with embodiments.

FIG. 6A illustrates an occlusal repositioning splint 630 shaped to fill an occlusal gap 650 between the upper and lower dentition of a patient. The occlusal repositioning splint 630 can form at least a portion of an appliance, said appliance comprising shell with a plurality of teeth receiving surfaces 620 shaped to receive a plurality of teeth 610 of a first arch. The occlusal splint can have an occlusal thickness 650 of varying occlusal thickness that extends across an occlusal plane defined by the teeth 610 towards an opposing arch. In some embodiments, the occlusal thickness 650 can extend across the occlusal plane an amount that varies along the length 640 of the occlusal repositioning splint, thereby presenting a variable surface to engage the opposing arch (or to engage an appliance worn on the opposing arch). In some embodiments, the occlusal thickness along the entire length of the occlusal repositioning splint can be equal to or approximately equal to the minimum distance between the occlusal surface of the tooth receiving structure and the corresponding engagement occlusal surface of the one or more teeth in the opposing arch, thereby filling a narrow gap between the upper and lower arches. In some embodiments, the distance between the surface of the tooth receiving structure and the corresponding engagement surface of the one or more teeth in the opposing arch can be variable for every position along the tooth receiving structure. In some embodiments, the occlusal thickness 650 of the occlusal repositioning splint can be arranged to provide a flat or substantially flat surface along at least a portion of the length 640, thereby providing greater freedom of motion to the opposing arch. The appliance can further comprise one or more tooth moving structures to apply tooth moving forces to one or more teeth (e.g., an extrusion, intrusion, translation, and/or rotation). These forces can be used to incrementally close an occlusal gap as a plurality of appliances is worn, and the occlusal repositioning splint can correspondingly be narrowed to bring the teeth into proper occlusion.

In some embodiments, the occlusal repositioning splint 630 has a bucco-lingual width of approximately the width of the patient's teeth. For example, the occlusal repositioning splint 630 can have a shape that follows at least a portion of the arch of the teeth 610. In some cases, the plurality of teeth receiving surfaces 620 can grip the teeth 610 of a first arch, and the opposing surface 660 of the occlusal repositioning splint can provide a lesser grip to teeth of the opposing arch, so that the splint remains attached to the first arch when the patient's mouth opens. In some cases, the teeth receiving surfaces 620 can be shaped to form teeth receiving cavities, and the opposing surface 660 can be shaped to provide an occlusal surface to mate with the opposing arch without significantly gripping the opposing arch. The surface 660 can be shaped to alter the natural occlusion of the upper and lower dentitions, thereby changing the natural bite of the patient. For example, the bite of the patient can be altered to shift the lower jaw forward or backward with respect to the upper jaw. More generally, the splint can urge movements in any direction to cause jaw movements from a first position and orientation (e.g., described in six degrees of freedom) along a path through subsequent positions and orientations toward a final position and orientation. Over time, this can produce changes in the positioning and orientation of the jaw as well as modifying the jaw musculature, which can result in a change in the patient's natural bite.

In some embodiments, the occlusal repositioning splint 630 is attached to an appliance that receives teeth 610 the patient's dentition. In some cases, the splint is integrally formed as part of the appliance. In other embodiments, the occlusal repositioning splint 630 is detachable from an appliance shaped to receive the teeth 610, and the splint is shaped to include a surface 620 to detachably mate with at least the occlusal side of the appliance.

In some embodiments, each of a plurality of occlusal repositioning splints can have an occlusal thickness equal to or approximately equal to the distance between the occlusal surface of a tooth receiving structure and the engagement occlusal surfaces of the one or more teeth in the opposing arch. Each of the plurality of occlusal repositioning splints can have an occlusal thickness that is uniform or variable. The thickness of each successive splint can change at one or more points along the occlusal repositioning splint. In some embodiments, the thickness of the occlusal repositioning splint can successively decrease among the plurality of appliances. In some embodiments, the thickness of the occlusal repositioning splint can successively increase among the plurality of appliances. In some embodiments, the thickness of the occlusal repositioning splint can be uniform among the plurality of appliances. In some embodiments, the thickness at each point along the occlusal repositioning splint can be the distance between the occlusal surface of the tooth receiving structure at each point and the corresponding engagement occlusal surface at each point in the opposing arch.

Figure 6B:
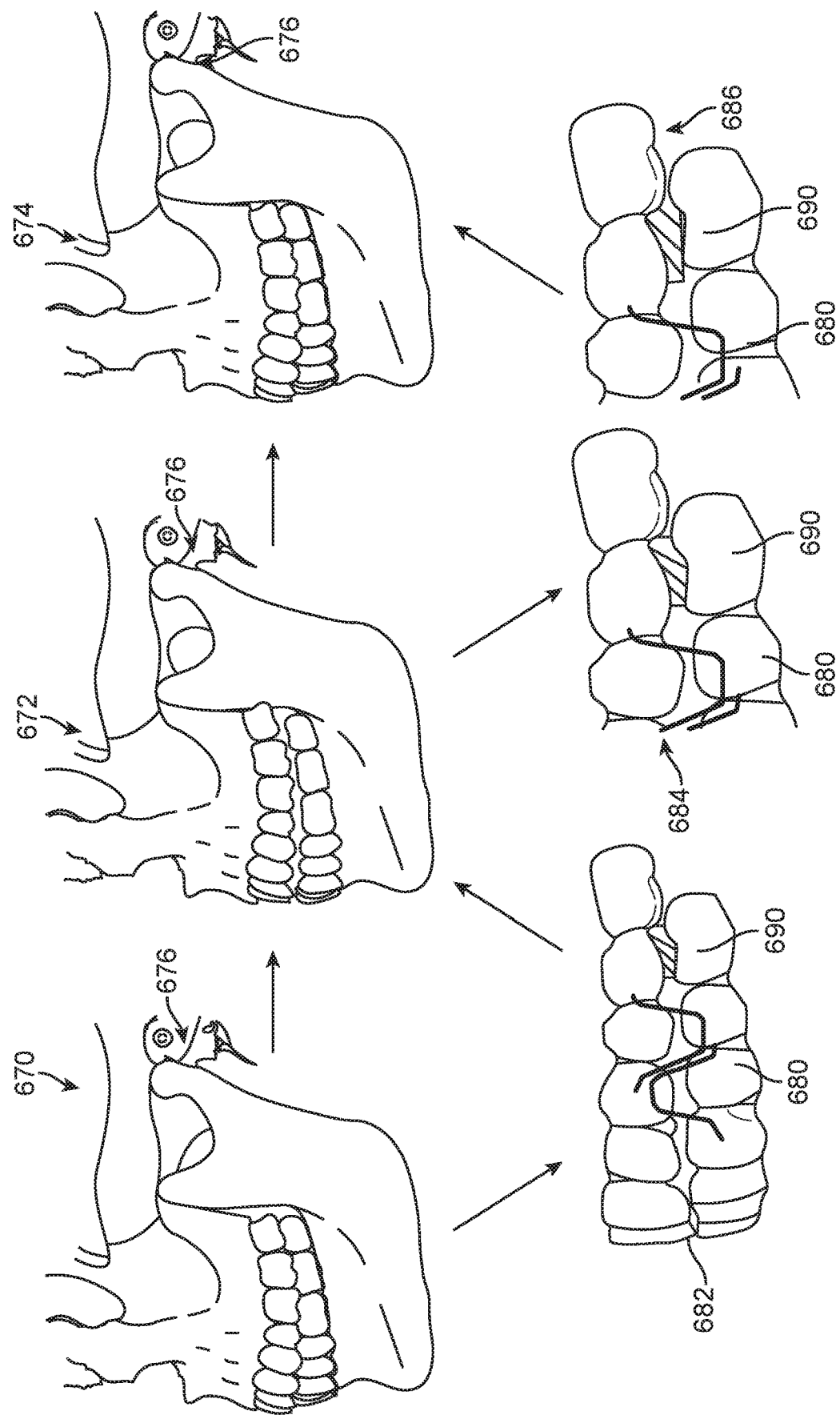
FIG. 6B illustrates a process of repositioning teeth and jaw, in accordance with embodiments.

FIG. 6B shows a process of correcting TMD by moving teeth and jaw. At stage 670, a patient's jaw and teeth are in a position indicating TMD. A first set of appliances may be applied to the patient's arches to correct the jaw to tooth positions to treat TMD. The appliances may include occlusal splints 690 and one or more mandibular positioning features 680 to correct the condylar position, the mandibular positions features may include precision wings, jaw stabilizers, intercuspation features, or a combination of two or more such features. An upper mandibular positions feature 680 may engage a lower mandibular positioning feature such that a condylar repositioning force is imparted to the lower jaw to advance the condylar position.

As treatment progresses, such as at stage 672, the jaw 676 may be in a corrected position, while the teeth may have yet to reach their final positions. Accordingly, the appliance set 684 may include mandibular positions features 680 and occlusal splints 690 to maintain the jaw position while the tooth alignment stages continue to move the teeth towards their final positions.

The position of the occlusal splints 690 may change between stages of treatment in order to maintain the position of the jaw form stage to stage while moving the teeth and jaw 676 to a final position, as indicated, for example at stage 674. For example, appliance set 686 includes a splint 690 that is located at a different occlusal position as compared to the position in appliance set 684. The shift in position accounts for the relative tooth movement between stages, such that the jaw position is maintained across stages.

In some embodiments the jaw and teeth are moved within the same set of treatment stages, in such embodiments the position, and movement thereof, of the mandibular position features and splints form stage to stage may account for both desired tooth movements and jaw movements over the set of treatment stages. Such a process may include determining new intercuspation positions for each stages, determining the jaw transformation or movement for the position, and then resolving these relative positions to determine the portion and geometries of mandibular positions features and splints in order to maintain or effect the prescribed movement of the jaw and teeth.

Lingual Repositioning Splint

In many embodiments, a method of moving teeth of a patient from first positions and orientations to second positions and orientations is provided. The method comprises successively providing a plurality of orthodontic appliances shaped to fit a plurality of teeth. In some embodiments, for each of the plurality of appliances the one or more teeth receiving structures includes lingual repositioning splint 700 extending lingually from the one or more tooth receiving structures.

Figure 7A:
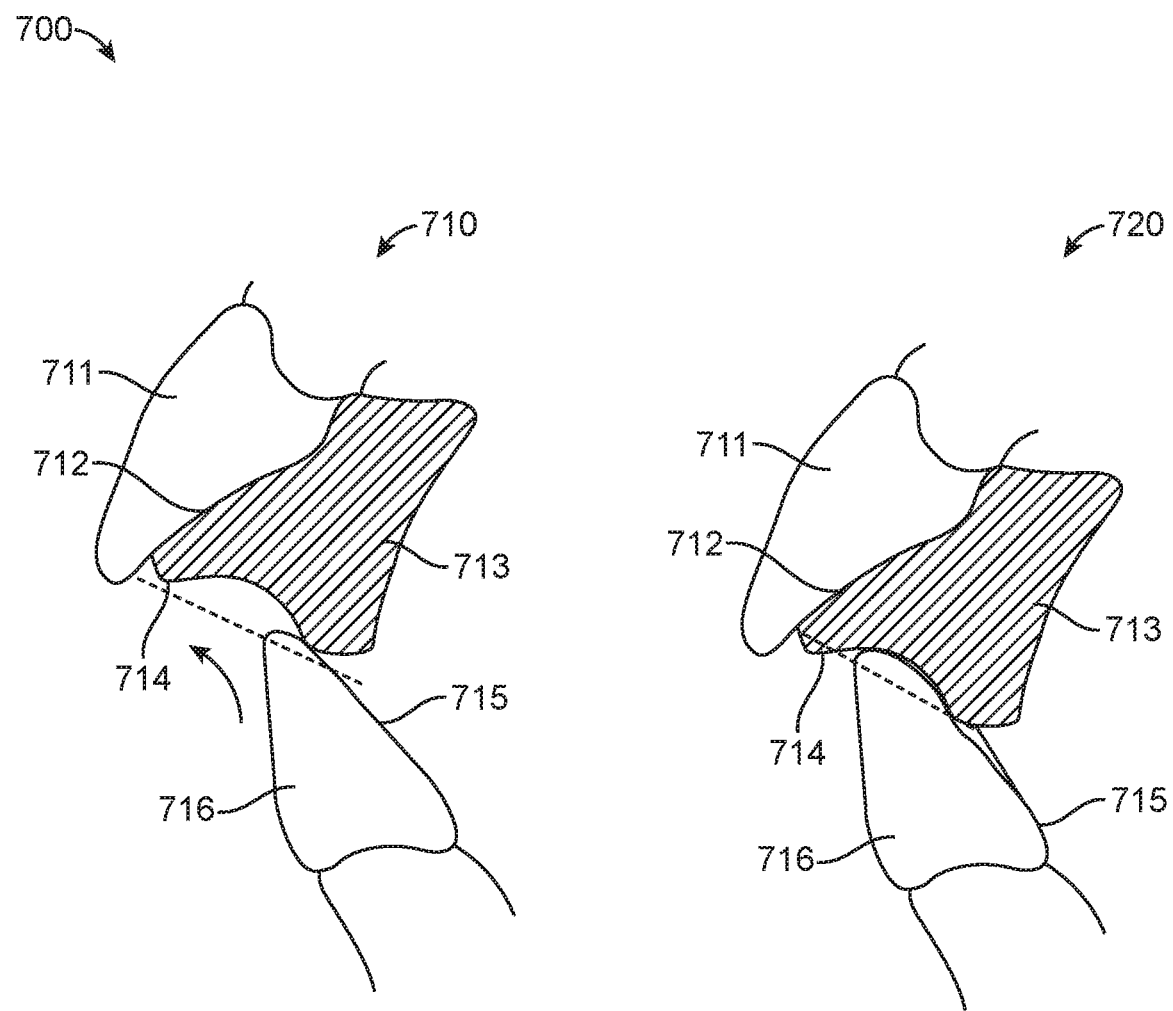
FIG. 7A illustrates a lingual repositioning splint located along the lingual side of the dental structure, in accordance with embodiments.

FIG. 7A illustrates a lingual repositioning splint 713 for moving a jaw from a first configuration 710 to a second configuration 720. When worn, the splint can be disposed on lingual surface 712 of tooth receiving structure 711 and can be comprise an occlusal surface 714 shaped to receive and guide engagement buccal surface 715 of the one or more teeth in opposing arch 716 from a first configuration 710 to a second configuration 720. For example, the occlusal surface 714 can include a curved shape to apply a force to the opposing arch when the arch is positioned away from a preferred position. Such a force can urge the patient's jaw to a different position, thereby providing improved intercuspation. For example, an overbite or underbite can be corrected by applying lingual repositioning splints to one or more incisors, with occlusal surfaces 714 shaped to guide the opposing arch into an improved position. More generally, the splint can urge movements in any direction to cause jaw movements from a first position and orientation (e.g., described in six degrees of freedom) along a path through subsequent positions and orientations toward a final position and orientation. Over time, this can produce changes in the positioning and orientation of the jaw as well as modifying the jaw musculature, which can result in a change in the patient's natural bite.

The lingual repositioning splint 713 can be shaped to alter the natural occlusion of the upper and lower dentitions, thereby changing the natural bite of the patient. For example, the bite of the patient can be altered to shift the lower jaw forward or backward with respect to the upper jaw. Over time, this can produce changes in the positioning of the jaw and of the jaw musculature, which can result in a change in the patient's natural bite.

In some embodiments, the lingual repositioning splint 713 is attached to an appliance that receives teeth 711 of the patient's dentition. In some cases, the splint is integrally formed as part of the appliance. In other embodiments, the lingual repositioning splint 713 is detachable from an appliance shaped to receive the teeth 711, and the splint is shaped to include surface 712 to detachably mate with at least the lingual side of the appliance.

Extended Lingual Repositioning Splint

Figure 7C:
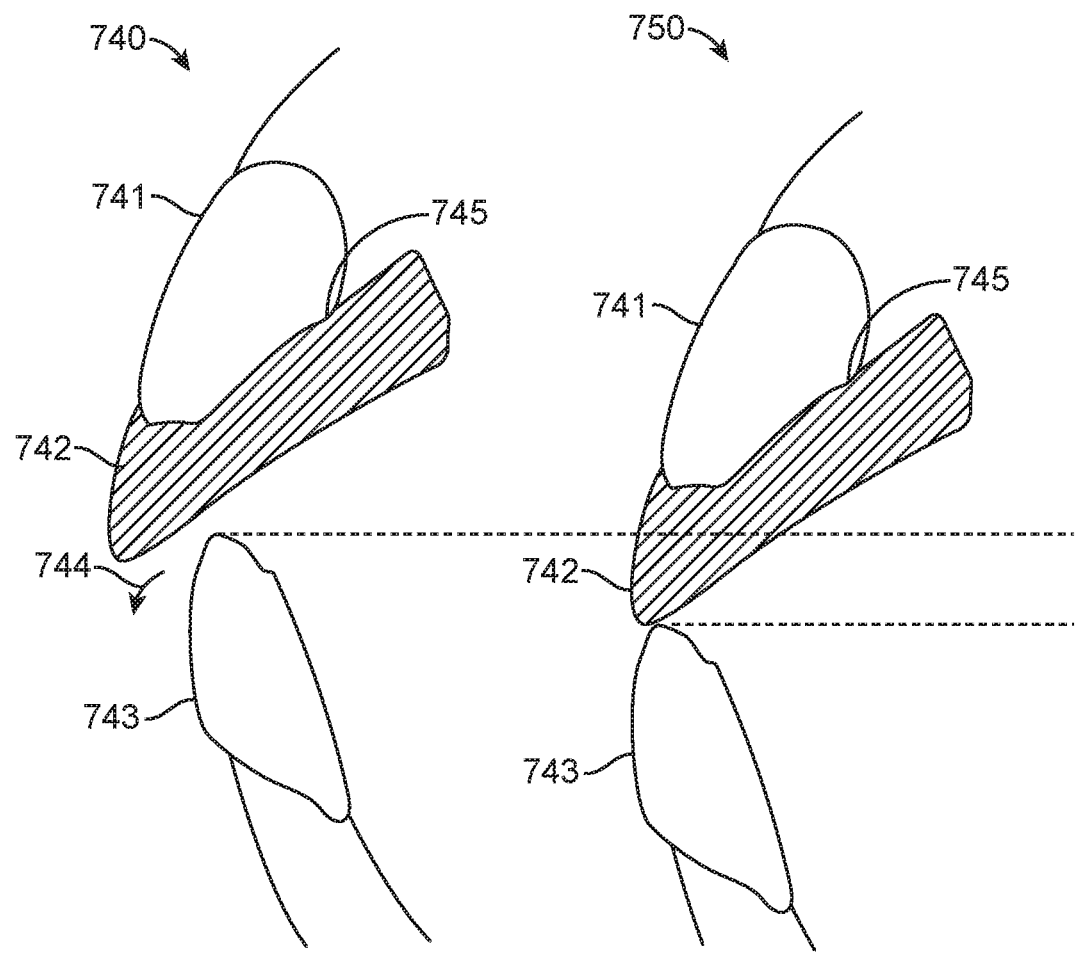
FIG. 7C illustrates a lingual repositioning splint located along the lingual side of the dental structure and the splint extends beyond the buccal side of the dental structure to create bite equilibrium, in accordance with embodiments.
Figure 8:
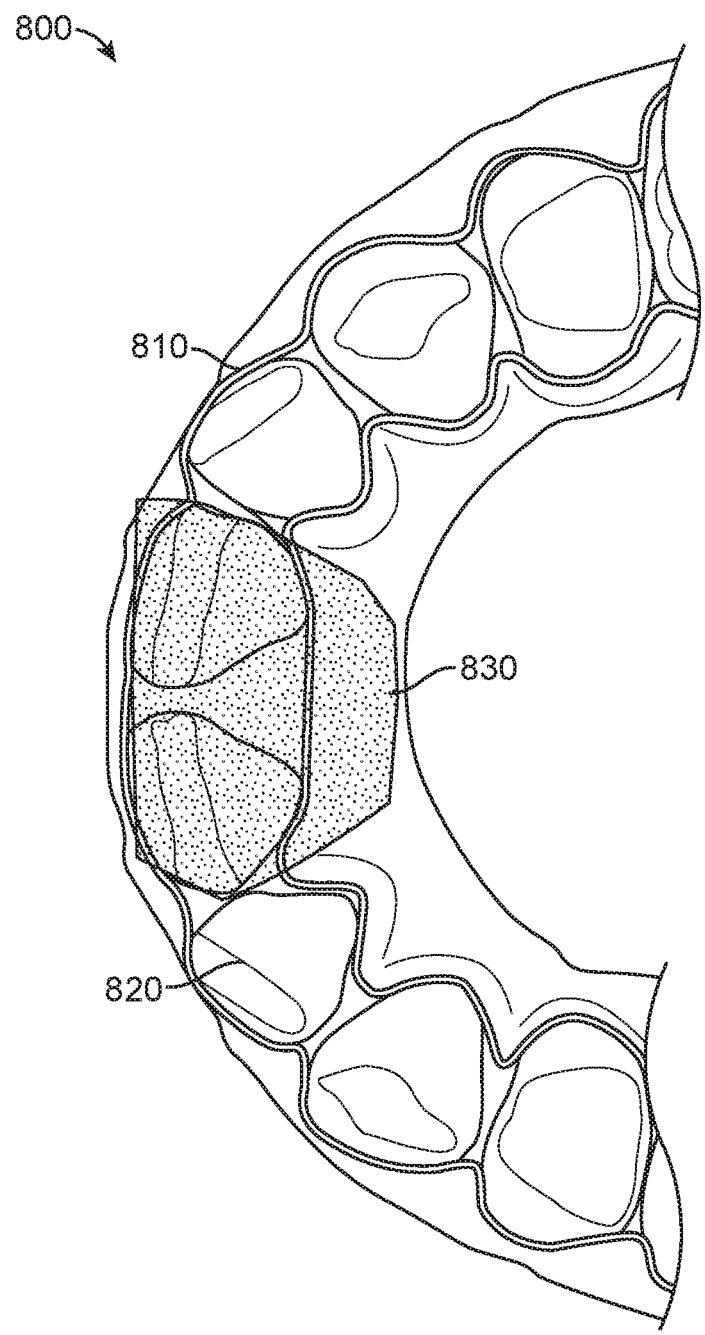
FIG. 8 illustrates a lingual repositioning splint disposed on the lingual side of a tooth may be used to apply opposing forces of any of the various structures described herein to create bite equilibrium, in accordance with embodiments.

In many embodiments, a method of moving teeth of a patient from first positions and orientations to second positions and orientations is provided. The method comprises successively providing a plurality of orthodontic appliances shaped to fit a plurality of teeth. As illustrated in FIG. 8, for each of the plurality of appliances the one or more teeth receiving structures 810 is coupled to extended lingual repositioning splint 830. In some embodiments, as illustrated in FIG. 7C, for each of the plurality of appliances the one or more teeth receiving structures is coupled to extended lingual repositioning splint 740 extending in lingual direction 744 from the one or more tooth receiving structures 741.

Figure 7B:
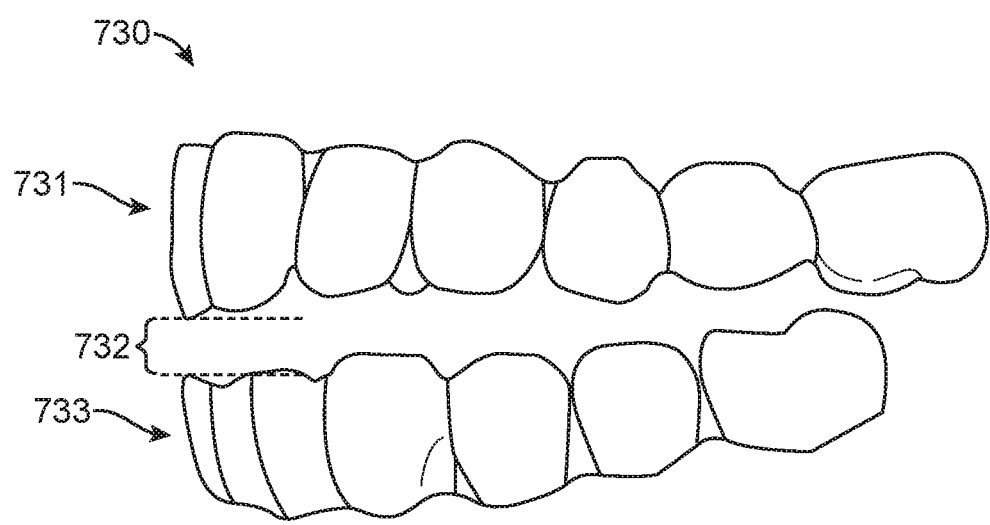
FIG. 7B illustrates the anterior open bite of a dental structure.

As illustrated in FIG. 7B, upper 731 and lower 732 arches of teeth of a patient may exhibit anterior open bite 732. When there is no guidance in the anterior teeth, the posterior teeth can experience interference during functional movements.

In some examples, the extended lingual repositioning splint can be coupled to the tooth receiving structure of the dorsal arch. In some examples, the extended lingual repositioning splint can be coupled to the tooth receiving structure of the ventral arch.

In some examples, the extended lingual repositioning splint 830 can be placed lingually on one or more teeth of dorsal arch 800 and can extend up to or beyond the buccal surface of one or more teeth of the ventral arch.

In some examples, the extended lingual repositioning splint can be placed lingually on one or more teeth of the ventral arch and can extend up to or beyond the buccal surface of one or more teeth of the dorsal arch.

The appliance can further comprise one or more tooth moving structures to apply tooth moving forces to one or more teeth (e.g., an extrusion, intrusion, translation, and/or rotation).

In many embodiments, for each of the plurality of appliances coupled to an extended lingual repositioning splint, the extended lingual repositioning splint can have a thickness equal to or approximately equal to the distance between the lingual surface of a tooth receiving structure and the engagement buccal surfaces of the one or more teeth in opposing arch 733. The thickness along the length of the lingual repositioning splint can be of one thickness or variable thickness. In some embodiments, the thickness along the entire length of the lingual repositioning splint can be equal to or approximately equal to the minimum distance between the lingual surface of the tooth receiving structure and the corresponding engagement buccal surface of the one or more teeth in the opposing arch. In some embodiments, the distance between the surface of the tooth receiving structure and the corresponding engagement surface of the one or more teeth in the opposing arch can be variable for every position along the tooth receiving structure.

FIG. 7C illustrates an extended lingual repositioning splint for moving a jaw from a first configuration 740 to a second configuration 750. When worn, the splint can be disposed on lingual surface 745 of tooth receiving structure 741 and can comprise a buccal surface 742 shaped to extend beyond the buccal surface of the one or more teeth in opposing arch 743. For example, the buccal surface 742 can engage with one or more teeth in the opposing arch to apply a force to the opposing arch. Such a force can urge the patient's jaw to a different position, thereby providing improved intercuspation. For example, an overbite or underbite can be corrected by applying extended lingual repositioning splints to one or more incisors, with buccal surfaces 742 shaped to guide the opposing arch into an improved position.

The extended lingual repositioning splint 742 can be shaped to alter the natural occlusion of the upper and lower dentitions, thereby changing the natural bite of the patient. For example, the bite of the patient can be altered to shift the lower jaw forward or backward with respect to the upper jaw. Over time, this can produce changes in the positioning of the jaw and of the jaw musculature, which can result in a change in the patient's natural bite.

In some embodiments, the extended lingual repositioning splint 742 is attached to an appliance that receives teeth 741 of the patient's dentition. In some cases, the splint is integrally formed as part of the appliance. In other embodiments, the extended lingual repositioning splint 742 is detachable from an appliance shaped to receive the teeth 741, and the splint is shaped to include a surface 745 to detachably mate with at least the lingual side of the appliance.

Engagement of Appliance with Tooth

In many embodiments, a plurality of orthodontic appliances is provided for moving one or more teeth of a patient from a first position and orientation to a second position and orientation. Each appliance comprises a plurality of teeth receiving cavities, an outer wall coupled to the teeth-receiving cavities and extending over buccal and lingual surfaces of the plurality of teeth, respectively, and a repositioning splint sized to enable bite equilibrium when the appliance is worn. The wall of the polymeric appliance can be shaped to receive one or more teeth and engage the one or more teeth.

In some embodiments, the appliance geometry comprises at least one repositioning splint configured to engage with the occlusal surfaces of one or more teeth in the opposing arch. The repositioning splint comprises a length extending the occlusal surfaces.

In some embodiments, the outer surface of the outer wall comprises a buccal surface of the appliance; in some embodiments, the outer surface of the outer wall comprises a lingual surface of the appliance.

In many embodiments, each repositioning splint is shaped to engage the occlusal surfaces of the opposing arch. In some embodiments, the repositioning splint is shaped to engage the occlusal surface of one or more teeth of the opposing arch. For example, the repositioning splint can engage one or more teeth of the opposing arch on either side of the mid-sagittal line. In another example, the repositioning splint can engage one or more teeth of the opposing arch on both sides of the mid-sagittal line.

In many embodiments, each repositioning splint is shaped to engage the occlusal surfaces of the opposing arch. The repositioning splint comprises a length extending the occlusal surfaces. One or more of the length or the width of the repositioning splint varies among the plurality of orthodontic appliances in order to create bite equilibrium when the plurality of appliances is worn in succession.

In some embodiments, each lingual repositioning splint comprises a contact surface having a length sized to engage one or more teeth of the opposing arch wherein the length of the contact surface varies among the plurality of appliances to vary the counter forces necessary to obtain bite equilibrium.

In many embodiments, a method of moving a tooth of patient from a first position and orientation to a second position and orientation is provided. The method comprises providing a polymeric shell appliance shaped to fit a plurality of teeth. The appliance comprises an outer wall shaped to extend over exposed buccal, lingual, and occlusal surfaces of the plurality of teeth and repositioning splint sized to enable bite equilibrium when the appliance is worn. The polymeric shell appliance is configured to contact at least about 60% of the circumferential surfaces of the plurality of teeth when worn. In some embodiments, the appliance contacts at least about 80% of the circumferential surface of the plurality of the teeth when worn.

In many embodiments, a method of moving a tooth of a patient from a first position and orientation to a second position and orientation is provided, comprising a plurality of orthodontic appliances shaped to fit a plurality of teeth. Each of the plurality of orthodontic appliances comprises a wall that is shaped to receive the plurality of teeth and a repositioning splint. The repositioning splint is sized to enable bite equilibrium and comprises a length along the occlusal surfaces of the arch when the appliance is worn in the mouth of the patient. One or more of the length or the thickness of the repositioning splint can vary among the plurality of orthodontic appliances in order to move the tooth from the first position and orientation to the second position and orientation when the plurality of appliances is worn in succession.

In some embodiments, the repositioning splint comprises a contact surface to engage one or more of the occlusal surfaces of the one or more teeth of the opposing arch wherein an angle of the contact surface varies among the plurality of appliances to create bite equilibrium while each appliance administers force to move the one or more teeth from the first location to the second location. In some embodiments, the repositioning splint comprises a contact surface having a length sized to engage one or more of the teeth and wherein the length of the contact surface varies among the plurality of appliances to vary the response to forces during jaw occlusal to create bite equilibrium.

In various embodiments, providing an orthodontic appliance comprises placing said appliance on the teeth of the patient. In various embodiments, the patient places the orthodontic appliance on the teeth.

In various embodiments, the tooth comprises a plurality of teeth.

In many embodiments, a polymeric shell appliance is provided for moving a tooth of a patient from a first position and orientation to a second position and orientation. The polymeric shell appliance comprises a polymeric lingual repositioning splint sized to extend across the occlusal surfaces of one or more teeth of the tooth receiving cavities. The repositioning splint is shaped to apply a counter force to the occlusal surfaces of one or more teeth of the opposing arch and move the tooth from the first position and orientation to the second position and orientation when the appliance is worn.

In many embodiments, a plurality of orthodontic appliances is provided for moving a tooth of a patient from a first position and orientation to a second position and orientation. Each appliance comprises a repositioning splint sized to extend across the occlusal surfaces of one or more teeth of the tooth receiving cavities in order to create bite equilibrium. A location of the repositioning splint relative to the one or more teeth receiving structures varies among the plurality of orthodontic appliances in order to create bite equilibrium while the appliances moves the tooth from the first position and orientation to the second position and orientation when the plurality of appliances are worn in succession.

Forces

Masticatory Force

Masticatory force is a force generated by the mastication muscles during the act of open and closing the jaw. The distribution of masticatory forces can differ. In some cases, masticatory forces can be maximal in the anterior dental arch. In some cases, masticatory forces can be maximal in the posterior. In some cases, maximum masticatory forces can be unilaterally distributed on the dental arch. Unilateral distribution can be on either side. In some cases, maximum masticatory forces can be bilaterally distributed on the dental arch. In some cases, maximum masticatory forces can be evenly distributed across the dental arches. In some cases, masticatory forces can be differentially distributed along the buccolingual axis. In some cases, masticatory forces can be even distributed along the buccolingual axis. In some cases, the distribution profile along the buccolingual axis can differ along the mesial-distal axis. In some cases, the distribution profile along the buccolingual axis can differ along the mesial-distal axis on either side of the mid-sagittal line.

In many embodiments, a plurality of orthodontic appliances is provided for moving a tooth of a patient from a first position and orientation to a second position and orientation. Each appliance comprises a repositioning splint sized to extend across the occlusal surfaces of one or more teeth of the tooth receiving cavities in order to create bite equilibrium. The repositioning splint applies counter forces equal to or approximately equal to the forces generated on the jaw from occlusion and apply a counter force to generate bite equilibrium. In many embodiments, the counter force is generated in all directions.

Forces for Tooth Movement

As used herein the terms "torque" and "moment" are treated synonymously.

As used herein the term "and/or" is used as a functional word to indicate that two words or expressions are to be taken together or individually. For example, A and/or B encompasses A alone, B alone, and A and B together.

As used herein a "moment" encompasses a force acting on an object such as a tooth at a distance from a center of resistance. The moment may be calculated with a vector cross product of a vector force applied to a location corresponding to a displacement vector from the center of resistance, for example. The moment may comprise a vector pointing in a direction. A moment opposing another moment may encompass one of the moment vectors oriented toward a first side of the object such as the tooth and the other moment vector oriented toward an opposite side of the object such as tooth, for example.

As used herein a "differential moment" encompasses two or more moments coupled to each other to provide opposing moments to one or more teeth. The differential moment may comprise a first moment and a second opposing moment applied to a tooth. Alternatively or in combination, the differential moment may comprise a first moment of a first one or more teeth of the arch coupled to a second, opposing moment of a second one or more teeth of the arch. The first one or more teeth of the arch may comprise a first segment of the arch and the second one or more teeth of the arch may comprise a second segment of the arch, in which the first moment of the first segment of the arch is coupled to the second, opposing moment of the second segment of the arch. The first one or more teeth may comprise a first plurality of adjacent teeth of the first segment of the arch, and the second one or more teeth may comprise a second plurality of adjacent teeth of the second segment of the arch, in which the first moment of the first plurality of adjacent teeth of the arch opposes the second, counter moment of the second plurality of adjacent teeth of the arch.

As used herein, a tooth comprising a moment refers to a tooth with a force acting on the tooth about a center of resistance. The force can be generated by an appliance coupled to the tooth, either directly or with an attachment on the tooth, and combinations thereof.

The counter moments as disclosed herein can be used to accurately control movement of one or more teeth, and can be used to provide anchoring of one or more teeth. In many embodiments, a plurality of posterior teeth comprise counter moments to improve anchoring of the posterior teeth, and one or more posterior teeth comprises a lesser counter movement and is moved toward the plurality of posterior anchor teeth. Alternatively, counter moments of one or more of the plurality posterior teeth can be configured to allow the one or more posterior teeth to move toward the anterior tooth.

The moments of a plurality of groups of one or more teeth can be coupled to each other in order to control movement of the teeth, and the moments of the one or more groups of teeth can be coupled to each other in many ways. The moments of the groups of one or more teeth can be coupled to each other with offset moments and/or balanced moments in order to provide preferential movement to one or more of the groups of one or more teeth. For example, posterior teeth can be provided with a larger counter moment than anterior teeth in order to move the anterior teeth to the posterior teeth.

The moments and counter moments as disclosed herein are well suited for moving many types of teeth and conditions of teeth, and are well suited for use with many conditions of teeth. The embodiments disclosed herein can be used to treat one or more of cant of an occlusal plane, to raise teeth on one side of the mouth and lower teeth on an opposite side of the mouth, en masse expansion of teeth along an arch, closure of an extraction site, intrusion, extrusion, rotation, tipping, and combinations thereof, for example.

In many embodiments, one or more posterior teeth comprises one or more of a molar, a premolar or a canine, and one or more anterior teeth comprising one or more of a central incisor, a lateral incisor, a cuspid, a first bicuspid or a second bicuspid.

The embodiments disclosed herein can be used to couple groups of one or more teeth to each other. The groups of one or more teeth may comprise a first group of one or more anterior teeth and a second group of one or more posterior teeth. The first group of teeth can be coupled to the second group of teeth with the polymeric shell appliances as disclosed herein.

The first group of teeth can be coupled to the second group of teeth in many ways, and in many embodiments the first group of one or more teeth comprises a first moment and a first counter moment, and the second group of one or more teeth comprises a second moment and a second counter moment. The first moment and the first counter moment may comprise a combined first moment and a combined first counter moment of the first group of one or more teeth, and the second moment and the second counter moment may comprise a combined second moment and a combined second counter moment of the second group of teeth. The combined first moment, combined first counter moment, combined second moment and combined second counter moment can be coupled to each other with the polymeric shell appliance in order to move the first group of one or more teeth or the second group of one or more teeth, and combinations thereof.

In many embodiments, each of the first group of one or more teeth comprises a first moment and a counter moment, and each of the second group of one or more teeth comprises a second moment and a second counter moment. The first moment can be generated with a first force to one or more of the first teeth at a first region or location of the first tooth and the counter moment generated with a counter force to the one of the first teeth at counter location. The second moment can be generated with a second force to one or more of the second teeth at a region of the second tooth and the counter moment generated with a counter force to the one of the second teeth at counter location.

The center of resistance of an individual tooth can be located near the bifurcation or trifurcation of the root of the tooth, for example. For a single rooted tooth, the center of resistance can be located somewhere between about 25% and about 70% of the distance from the alveolar crest to the apex of the root, for example about 40% of the distance.

The center of resistance of a group of a segment of teeth comprising a plurality of teeth can be determined in one or more of many ways. The center of resistance can be determined with finite element modeling, published values in the scientific literature, bench testing with experimental loads, mathematical formula and approximations, and combinations thereof, for example. The center of resistance can be determined in response to supporting dental structures such as the periodontal ligaments, soft tissue, and bony supporting structures, for example. Although the center of resistance of a group of teeth may change with the direction of movement, a person of ordinary skill in the art can determine the center of resistance in accordance with embodiments disclosed herein.

The embodiments disclosed herein are well suited for moving one or more teeth of the first group of one or more teeth or moving one or more of the second group of one or more teeth, and combinations thereof.

The embodiments disclosed herein are well suited for combination with one or more known commercially available tooth moving components such as attachments and polymeric shell appliances. In many embodiments, the appliance and one or more attachments are configured to move one or more teeth along a tooth movement vector comprising six degrees of freedom, in which three degrees of freedom are rotational and three degrees of freedom are translation. Embodiments disclosed herein can provide differential moment vectors based on a moment and a counter moment to each of a plurality of teeth. The differential moment vector can provide improved accuracy of movement of the teeth and may result in decreased amounts of force to move one or more teeth.

The present disclosure provides orthodontic systems and related methods for designing and providing improved or more effective tooth moving systems for eliciting a desired tooth movement and/or repositioning teeth into a desired arrangement.

In various embodiments, at least one appliance comprises a plurality of materials.

In various embodiments, at least one appliance comprises a plurality of materials. In various embodiments, the appliance is configured to be manually removable by the patient.

In some embodiments, one or more of the repositioning splints comprises material to resiliently deform or deflect in response to forces from the teeth.

Although reference is made to an appliance comprising a polymeric shell appliance, the embodiments disclosed herein are well suited for use with many appliances that receive teeth, for example appliances without one or more of polymers or shells. The appliance can be fabricated with one or more of many materials such as metal, glass, reinforced fibers, carbon fiber, composites, reinforced composites, aluminum, biological materials, and combinations thereof for example. The appliance can be shaped in many ways, such as with thermoforming or direct fabrication as described herein, for example. Alternatively or in combination, the appliance can be fabricated with machining such as an appliance fabricated from a block of material with computer numeric control machining.

Tooth Movement

In some embodiments, the plurality of movements can comprise one or more of a translation or a rotation about a center of rotation of one or more teeth.

In various embodiments, moving the one or more teeth comprises a translation of the one or more teeth. In some embodiments, moving the one or more teeth comprises a rotation the one or more teeth. In some embodiments, the rotation comprises a rotation about a vertical axis. In some embodiments, the rotation comprises a rotation about a buccolingual axis.

In some embodiments, the plurality of movements comprises successive rotations of one or more of the teeth about an axis of rotation extending through a center of rotation and an occlusal surface of the one or more teeth.

In some embodiments, the appliances are configured to produce a movement of the teeth when worn successively, the movement comprising one or more of a translation or a rotation, and wherein the plurality of distances decreases in accordance with movement of the teeth. In some cases, the appliances are configured to produce a translation of the teeth when worn successively, and wherein the plurality of distances decreases in accordance with translation of one or more teeth. In some cases, the appliances are configured to produce a rotation of the teeth when worn successively, and wherein the plurality of distances decreases in accordance with rotation of one or more teeth about a center of rotation.

In some embodiments, the appliances are configured to produce a rotation of the teeth when worn successively, and wherein the plurality of distances successively decreases in accordance with successive rotations of one or more of the teeth about an axis of rotation extending through a center of rotation and an occlusal surface of the one or more teeth.

Fabrication

The various embodiments of the orthodontic appliances presented herein can be fabricated in a wide variety of ways. In some embodiments, the method further comprises manufacturing a plurality of orthodontic appliances, each of the plurality of orthodontic appliances configured to produce a movement along the movement path.

In some embodiments, the orthodontic appliances herein (or portions thereof) can be produced using direct fabrication, such as additive manufacturing techniques (also referred to herein as "3D printing) or subtractive manufacturing techniques (e.g., milling).

In some embodiments, direct fabrication involves forming an object (e.g., an orthodontic appliance or a portion thereof) without using a physical template (e.g., mold, mask etc.) to define the object geometry. Additive manufacturing techniques can be categorized as follows: (1) vat photopolymerization (e.g., stereolithography), in which an object is constructed layer by layer from a vat of liquid photopolymer resin; (2) material jetting, in which material is jetted onto a build platform using either a continuous or drop on demand (DOD) approach; (3) binder jetting, in which alternating layers of a build material (e.g., a powder-based material) and a binding material (e.g., a liquid binder) are deposited by a print head; (4) fused deposition modeling (FDM), in which material is drawn though a nozzle, heated, and deposited layer by layer; (5) powder bed fusion, including but not limited to direct metal laser sintering (DMLS), electron beam melting (EBM), selective heat sintering (SHS), selective laser melting (SLM), and selective laser sintering (SLS); (6) sheet lamination, including but not limited to laminated object manufacturing (LOM) and ultrasonic additive manufacturing (UAM); and (7) directed energy deposition, including but not limited to laser engineering net shaping, directed light fabrication, direct metal deposition, and 3D laser cladding. For example, stereolithography can be used to directly fabricate one or more of the appliances herein. In some embodiments, stereolithography involves selective polymerization of a photosensitive resin (e.g., a photopolymer) according to a desired cross-sectional shape using light (e.g., ultraviolet light). The object geometry can be built up in a layer-by-layer fashion by sequentially polymerizing a plurality of object cross-sections. As another example, the appliances herein can be directly fabricated using selective laser sintering. In some embodiments, selective laser sintering involves using a laser beam to selectively melt and fuse a layer of powdered material according to a desired cross-sectional shape in order to build up the object geometry. As yet another example, the appliances herein can be directly fabricated by fused deposition modeling. In some embodiments, fused deposition modeling involves melting and selectively depositing a thin filament of thermoplastic polymer in a layer-by-layer manner in order to form an object. In yet another example, material jetting can be used to directly fabricate the appliances herein. In some embodiments, material jetting involves jetting or extruding one or more materials onto a build surface in order to form successive layers of the object geometry.

Alternatively or in combination, some embodiments of the appliances herein (or portions thereof) can be produced using indirect fabrication techniques, such as by thermoforming over a positive or negative mold. Indirect fabrication of an orthodontic appliance can involve producing a positive or negative mold of the patient's dentition in a target arrangement (e.g., by rapid prototyping, milling, etc.) and thermoforming one or more sheets of material over the mold in order to generate an appliance shell.

In some embodiments, the direct fabrication methods provided herein build up the object geometry in a layer-by-layer fashion, with successive layers being formed in discrete build steps. Alternatively or in combination, direct fabrication methods that allow for continuous build-up of an object geometry can be used, referred to herein as "continuous direct fabrication." Various types of continuous direct fabrication methods can be used. As an example, in some embodiments, the appliances herein are fabricated using "continuous liquid interphase printing," in which an object is continuously built up from a reservoir of photopolymerizable resin by forming a gradient of partially cured resin between the building surface of the object and a polymerization-inhibited "dead zone." In some embodiments, a semi-permeable membrane is used to control transport of a photopolymerization inhibitor (e.g., oxygen) into the dead zone in order to form the polymerization gradient. Continuous liquid interphase printing can achieve fabrication speeds about 25 times to about 100 times faster than other direct fabrication methods, and speeds about 1000 times faster can be achieved with the incorporation of cooling systems. Continuous liquid interphase printing is described in U.S. Patent Publication Nos. 2015/0097315, 2015/0097316, and 2015/0102532, the disclosures of each of which are incorporated herein by reference in their entirety.

As another example, a continuous direct fabrication method can achieve continuous build-up of an object geometry by continuous movement of the build platform (e.g., along the vertical or Z-direction) during the irradiation phase, such that the hardening depth of the irradiated photopolymer is controlled by the movement speed. Accordingly, continuous polymerization of material on the build surface can be achieved. Such methods are described in U.S. Pat. No. 7,892,474, the disclosure of which is incorporated herein by reference in its entirety.

In another example, a continuous direct fabrication method can involve extruding a composite material composed of a curable liquid material surrounding a solid strand. The composite material can be extruded along a continuous three-dimensional path in order to form the object. Such methods are described in U.S. Patent Publication No. 2014/0061974, the disclosure of which is incorporated herein by reference in its entirety.

In yet another example, a continuous direct fabrication method utilizes a "heliolithography" approach in which the liquid photopolymer is cured with focused radiation while the build platform is continuously rotated and raised. Accordingly, the object geometry can be continuously built up along a spiral build path. Such methods are described in U.S. Patent Publication No. 2014/0265034, the disclosure of which is incorporated herein by reference in its entirety.

The direct fabrication approaches provided herein are compatible with a wide variety of materials, including but not limited to one or more of the following: a polyester, a co-polyester, a polycarbonate, a thermoplastic polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, a polytrimethylene terephthalate, a styrenic block copolymer (SBC), a silicone rubber, an elastomeric alloy, a thermoplastic elastomer (TPE), a thermoplastic vulcanizate (TPV) elastomer, a polyurethane elastomer, a block copolymer elastomer, a polyolefin blend elastomer, a thermoplastic co-polyester elastomer, a thermoplastic polyamide elastomer, or combinations thereof. The materials used for direct fabrication can be provided in an uncured form (e.g., as a liquid, resin, powder, etc.) and can be cured (e.g., by photopolymerization, light curing, gas curing, laser curing, crosslinking, etc.) in order to form an orthodontic appliance or a portion thereof. The properties of the material before curing may differ from the properties of the material after curing. Once cured, the materials herein can exhibit sufficient strength, stiffness, durability, biocompatibility, etc. for use in an orthodontic appliance. The post-curing properties of the materials used can be selected according to the desired properties for the corresponding portions of the appliance.

In some embodiments, relatively rigid portions of the orthodontic appliance can be formed via direct fabrication using one or more of the following materials: a polyester, a co-polyester, a polycarbonate, a thermoplastic polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, and/or a polytrimethylene terephthalate.

As used herein the terms "stiff" and "rigid" are used interchangeably.

In some embodiments, relatively elastic portions of the orthodontic appliance can be formed via direct fabrication using one or more of the following materials: a styrenic block copolymer (SBC), a silicone rubber, an elastomeric alloy, a thermoplastic elastomer (TPE), a thermoplastic vulcanizate (TPV) elastomer, a polyurethane elastomer, a block copolymer elastomer, a polyolefin blend elastomer, a thermoplastic co-polyester elastomer, and/or a thermoplastic polyamide elastomer.

Machine parameters can include curing parameters. For digital light processing (DLP)-based curing systems, curing parameters can include power, curing time, and/or grayscale of the full image. For laser-based curing systems, curing parameters can include power, speed, beam size, beam shape and/or power distribution of the beam. For printing systems, curing parameters can include material drop size, viscosity, and/or curing power. These machine parameters can be monitored and adjusted on a regular basis (e.g., some parameters at every 1-x layers and some parameters after each build) as part of the process control on the fabrication machine. Process control can be achieved by including a sensor on the machine that measures power and other beam parameters every layer or every few seconds and automatically adjusts them with a feedback loop. For DLP machines, gray scale can be measured and calibrated before, during, and/or at the end of each build, and/or at predetermined time intervals (e.g., every $n^{th}$ build, once per hour, once per day, once per week, etc.), depending on the stability of the system. In addition, material properties and/or photo-characteristics can be provided to the fabrication machine, and a machine process control module can use these parameters to adjust machine parameters (e.g., power, time, gray scale, etc.) to compensate for variability in material properties. By implementing process controls for the fabrication machine, reduced variability in appliance accuracy and residual stress can be achieved.

Optionally, the direct fabrication methods described herein allow for fabrication of an appliance including multiple materials, referred to herein as "multi-material direct fabrication." In some embodiments, a multi-material direct fabrication method involves concurrently forming an object from multiple materials in a single manufacturing step. For instance, a multi-tip extrusion apparatus can be used to selectively dispense multiple types of materials (e.g., resins, liquid, solids, or combinations thereof) from distinct material supply sources in order to fabricate an object from a plurality of different materials. Such methods are described in U.S. Pat. No. 6,749,414, the disclosure of which is incorporated herein by reference in its entirety. Alternatively or in combination, a multi-material direct fabrication method can involve forming an object from multiple materials in a plurality of sequential manufacturing steps. For instance, a first portion of the object (e.g., an appliance shell) can be formed from a first material in accordance with any of the direct fabrication methods herein, then a second portion of the object (e.g., one or more elastics) can be formed from a second material in accordance with methods herein, and so on, until the entirety of the object has been formed. The relative arrangement of the first and second portions can be varied as desired, e.g., the first portion can be partially or wholly encapsulated by the second portion of the object.

Direct fabrication can provide various advantages compared to other manufacturing approaches. For instance, in contrast to indirect fabrication, direct fabrication permits production of an orthodontic appliance without utilizing any molds or templates for shaping the appliance, thus reducing the number of manufacturing steps involved and improving the resolution and accuracy of the final appliance geometry. Additionally, direct fabrication permits precise control over the three-dimensional geometry of the appliance, such as the appliance thickness. Complex structures and/or auxiliary components can be formed integrally as a single piece with the appliance shell in a single manufacturing step, rather than being added to the shell in a separate manufacturing step. In some embodiments, direct fabrication is used to produce appliance geometries that would be difficult to create using alternative manufacturing techniques, such as appliances with very small or fine features, complex geometric shapes, undercuts, interproximal structures, shells with variable thicknesses, and/or internal structures (e.g., for improving strength with reduced weight and material usage). For example, in some embodiments, the direct fabrication approaches herein permit fabrication of an orthodontic appliance with feature sizes of less than or equal to about 5 µm, or within a range from about 5 µm to about 50 µm, or within a range from about 20 µm to about 50 µm.

The direct fabrication techniques described herein can be used to produce appliances with substantially isotropic material properties, e.g., substantially the same or similar strengths along all directions. In some embodiments, the direct fabrication approaches herein permit production of an orthodontic appliance with a strength that varies by no more than about 25%, about 20%, about 15%, about 10%, about 5%, about 1%, or about 0.5% along all directions. Additionally, the direct fabrication approaches herein can be used to produce orthodontic appliances at a faster speed compared to other manufacturing techniques. In some embodiments, the direct fabrication approaches herein allow for production of an orthodontic appliance in a time interval less than or equal to about 1 hour, about 30 minutes, about 25 minutes, about 20 minutes, about 15 minutes, about 10 minutes, about 5 minutes, about 4 minutes, about 3 minutes, about 2 minutes, about 1 minutes, or about 30 seconds. Such manufacturing speeds allow for rapid "chair-side" production of customized appliances, e.g., during a routine appointment or checkup.

In some embodiments, the direct fabrication methods described herein implement process controls for various machine parameters of a direct fabrication system or device in order to ensure that the resultant appliances are fabricated with a high degree of precision. Such precision can be beneficial for ensuring accurate delivery of a desired force system to the teeth in order to effectively elicit tooth movements. Process controls can be implemented to account for process variability arising from multiple sources, such as the material properties, machine parameters, environmental variables, and/or post-processing parameters.

Material properties may vary depending on the properties of raw materials, purity of raw materials, and/or process variables during mixing of the raw materials. In many embodiments, resins or other materials for direct fabrication should be manufactured with tight process control to ensure little variability in photo-characteristics, material properties (e.g., viscosity, surface tension), physical properties (e.g., modulus, strength, elongation) and/or thermal properties (e.g., glass transition temperature, heat deflection temperature). Process control for a material manufacturing process can be achieved with screening of raw materials for physical properties and/or control of temperature, humidity, and/or other process parameters during the mixing process. By implementing process controls for the material manufacturing procedure, reduced variability of process parameters and more uniform material properties for each batch of material can be achieved. Residual variability in material properties can be compensated with process control on the machine, as discussed further herein.

Machine parameters can include curing parameters. For digital light processing (DLP)-based curing systems, curing parameters can include power, curing time, and/or grayscale of the full image. For laser-based curing systems, curing parameters can include power, speed, beam size, beam shape and/or power distribution of the beam. For printing systems, curing parameters can include material drop size, viscosity, and/or curing power. These machine parameters can be monitored and adjusted on a regular basis (e.g., some parameters at every 1-x layers and some parameters after each build) as part of the process control on the fabrication machine. Process control can be achieved by including a sensor on the machine that measures power and other beam parameters every layer or every few seconds and automatically adjusts them with a feedback loop. For DLP machines, gray scale can be measured and calibrated at the end of each build. In addition, material properties and/or photo-characteristics can be provided to the fabrication machine, and a machine process control module can use these parameters to adjust machine parameters (e.g., power, time, gray scale, etc.) to compensate for variability in material properties. By implementing process controls for the fabrication machine, reduced variability in appliance accuracy and residual stress can be achieved.

In many embodiments, environmental variables (e.g., temperature, humidity, Sunlight or exposure to other energy/curing source) are maintained in a tight range to reduce variable in appliance thickness and/or other properties. Optionally, machine parameters can be adjusted to compensate for environmental variables.

In many embodiments, post-processing of appliances includes cleaning, post-curing, and/or support removal processes. Relevant post-processing parameters can include purity of cleaning agent, cleaning pressure and/or temperature, cleaning time, post-curing energy and/or time, and/or consistency of support removal process. These parameters can be measured and adjusted as part of a process control scheme. In addition, appliance physical properties can be varied by modifying the post-processing parameters. Adjusting post-processing machine parameters can provide another way to compensate for variability in material properties and/or machine properties.

What is claimed is:

1. A method for digitally designing a plurality of appliances for treating or preventing temporomandibular joint dysfunction (TMD), the method comprising:
   - obtaining first bite scan data of a dentition of a patient with the patient's jaws in a target bite configuration;
   - obtaining second bite scan data of the dentition of the patient with the patient's jaws in a natural bite configuration; and
   - identifying a sequence of incremental arrangements for the dentition as part of an orthodontic treatment, wherein the sequence of incremental arrangements are configured to move the dentition from the natural bite configuration toward the target bite configuration;
   - determining one or more occlusal gaps between upper teeth of the dentition and lower teeth of the dentition present during each of the incremental arrangements, wherein the one or more occlusal gaps further relate to TMD in the natural bite configuration;
   - identifying one or more pairs of occlusal surfaces features extending from occlusal surfaces of the upper teeth and the lower teeth, respectively, wherein the one or more pairs of occlusal surface features are sequentially repositioned through the sequence of incremental arrangements to fill the one or more occlusal gaps between the upper teeth and the lower teeth throughout the course of the orthodontic treatment, and wherein the one or more pairs of occlusal surface features are configured to move at least a portion of the upper teeth of the dentition and at least a portion of the lower teeth of the dentition closer to one another, thereby narrowing at least part of the one or more occlusal gaps; and
   - incorporating the one or more pairs of occlusal surface features into geometries of the plurality of appliances at corresponding stages of the sequence of incremental arrangements to move the dentition from the natural bite configuration toward the target bite configuration through the sequence of incremental arrangements and manufacturing the plurality of appliances.

2. The method of claim 1, wherein obtaining the first bite scan data comprises scanning the dentition of the patient in the target bite configuration and obtaining the second bite scan data comprises scanning the dentition of the patient in the natural bite configuration.

3. The method of claim 1, further comprising providing the plurality of appliances to the patient.

4. The method of claim 3, further comprising placing at least one of the plurality of appliances on the dentition of the patient.

5. The method of claim 1 wherein each of the plurality of appliances comprises a polymeric shell.

6. The method of claim 1, wherein each of the plurality of appliances comprises a first polymeric shell shaped to receive the upper teeth of the dentition and a second polymeric shell shaped to receive the lower teeth of the dentition.

7. The method of claim 1, the method further comprising selecting an incremental arrangement in the sequence of incremental arrangements as a final bite configuration, wherein the final bite configuration is different relative to the target bite configuration.

8. The method of claim 7, wherein the final bite configuration is selected to avoid one or more lower-to-upper teeth collisions present in the target bite configuration.

9. The method of claim 1, wherein at least one of the plurality of appliances is a removable appliance.

10. The method of claim 1, wherein a position of at least one of the one or more occlusal surface features differs between a first of the plurality of appliances and a second of the appliances.

11. The method of claim 1, wherein the one or more occlusal gaps comprises a gap between opposing molars or opposing premolars.

12. The method of claim 1, wherein each incremental arrangement in the sequence of incremental arrangements comprises tooth contact paths for each of a plurality of teeth, and wherein designing the plurality of appliances comprises optimizing the tooth contact paths for the incremental steps to avoid tooth collisions during the incremental steps.

* * * * *